US009080170B2

(12) United States Patent
Garcia et al.

(10) Patent No.: US 9,080,170 B2
(45) Date of Patent: Jul. 14, 2015

(54) MODIFIED U7 SNRNAS FOR TREATMENT OF NEUROMUSCULAR DISEASES

(75) Inventors: Luis Garcia, Bailly (FR); Denis Furling, Champigny-sur-Marne (FR); Cyriaque Beley, Fontenay le Fleury (FR); Thomas Voit, Boullay-les Troux (FR)

(73) Assignee: ASSOCIATION INSTITUT DE MYOLOGIE, Paris (FR)

( * ) Notice: Subject to any disclaimer, the term of this patent is extended or adjusted under 35 U.S.C. 154(b) by 0 days.

(21) Appl. No.: 13/635,356

(22) PCT Filed: Mar. 17, 2011

(86) PCT No.: PCT/EP2011/054026
§ 371 (c)(1),
(2), (4) Date: Nov. 7, 2012

(87) PCT Pub. No.: WO2011/113889
PCT Pub. Date: Sep. 22, 2011

(65) Prior Publication Data
US 2013/0045538 A1      Feb. 21, 2013

Related U.S. Application Data

(60) Provisional application No. 61/314,830, filed on Mar. 17, 2010.

(51) Int. Cl.
*C07H 21/04* (2006.01)
*C12N 15/11* (2006.01)

(52) U.S. Cl.
CPC .......... *C12N 15/111* (2013.01); *C12N 2310/11* (2013.01); *C12N 2320/33* (2013.01); *C12N 2320/34* (2013.01); *C12N 2330/51* (2013.01)

(58) Field of Classification Search
CPC .......................... C12N 15/111; C12N 2310/11
See application file for complete search history.

(56) References Cited

U.S. PATENT DOCUMENTS

| 2003/0036519 | A1 | 2/2003 | Kole et al. |
| 2003/0114411 | A1 | 6/2003 | Kole et al. |
| 2012/0077860 | A1* | 3/2012 | Garcia .................. 514/44 A |

FOREIGN PATENT DOCUMENTS

WO        2006021724   A2     3/2006

OTHER PUBLICATIONS

International Search Report for PCT/EP2011/054026 mailed June 30, 2011.

* cited by examiner

*Primary Examiner* — Kimberly Chong
(74) *Attorney, Agent, or Firm* — Miles & Stockbridge P.C.

(57) ABSTRACT

The present invention relates to a method to improve the activity of engineered U7 snRNAs used in the context of RNA-based therapeutics; particularly in exon skipping, exon inclusion, and mRNA eradication strategies. The resulting modified U7 snRNAs are useful for treating neuromuscular diseases, in particular Duchenne neuromuscular dystrophy, myotonic dystrophy DM1 and spinal muscular atrophy.

24 Claims, 11 Drawing Sheets

TACTGCCGAATCCAGGTCTCCGGGCT
TAACAACGAAGGGGCTGTGACTG
GCTGCTTTCTCAACCAATCAGCACCGA
ACTCATTTGCATGGGCTGAGAACAAAT
GTTCGCGAACTCTAGAAATGAATGACT
TAAGTAAGTTCCTTAGAATATTATTTTC
CTACTGAAAGTTACCACATGCGTCGTT
GTTTATACAGTAATAGGAACAAGAAAAA
AGTCACCTAAGCTCACCCTCATCAATT
GTGGAGTTCCTTTATATCCCATCTTCTC
TCCAAACACATACGCACAGCAGCAGC
AGCAGCAGCAGCAGCAGCAGCAGCA
GCAGCAGCAGAATTTTGGAGTAGGC
TTTCTGGCTTTTTACCGGAAAGCCCCT
CTTATGATGTTTGTTGCCAATGATAGAT
TGTTTTCACTGTGCAAAAATTATGGGTA
GTTTTGGTGGTCTTGATGCAGTTGTAA
GCTTGGAG

MODIFIED U7 SNRNAS FOR TREATMENT OF NEUROMUSCULAR DISEASES

CROSS REFERENCE TO RELATED APPLICATIONS

This application is a §371 National Stage Application of PCT/EP2011/054026 filed Mar. 17, 2011, which claims priority to U.S. Provisional Application No. 61/314,830 filed Mar. 17, 2010, the content of which is incorporated herein by reference in its entirety.

BACKGROUND OF THE INVENTION

1. Field of the Invention

The present invention relates to a method to improve the activity of engineered U7 snRNAs used in the context of RNA-based therapeutics; particularly in exon skipping, exon inclusion, and mRNA eradication strategies.

2. Description of Related Arts

Conventional gene therapy has focused largely on gene replacement in target cells. RNA-based strategies offer a series of novel therapeutic applications, including altered processing of the target pre-mRNA transcript, reprogramming of genetic defects through mRNA repair, and the targeted silencing of allele- or isoform-specific gene transcripts. Similarly, in disorders of RNA processing, such as aberrant splicing, it may be preferable to repair the endogenous splicing pattern, which could also correct multiple alternative isoforms.

Many genes use alternative splicing to generate multiple gene products. Being able to modulate the splicing pathway of a particular gene (on demand alternative splicing) has many potential applications in the field of gene therapy. For instance, the forced skipping of a precise exon might be used to inhibit gene function or to promote synthesis of an internally deleted or truncated protein, depending on whether the remaining exons are fused in- or out-of-frame. Similarly, forced inclusion of an exon, which is abnormally spliced from the final mRNA, would also be clinically relevant in many pathological inherited conditions.

Neuromuscular disease refers to a group of hereditary muscle diseases that weaken the muscles that move the human body. They include such diseases as e.g. neuromuscular dystrophies and spinal muscular atrophy. Nine diseases including Duchenne, Becker, limb girdle, congenital, facioscapulohumeral, myotonic, oculopharyngeal, distal, and Emery-Dreifuss are always classified as neuromuscular dystrophy but there are more than 100 diseases in total with similarities to neuromuscular dystrophy. These conditions have a genetic basis, and the different genetic muscular diseases follow various inheritance patterns. The best-known type, Duchenne neuromuscular dystrophy (DMD), is a severe recessive X-linked form characterized by the absence of a 427 kDa protein denominated dystrophin. The absence of a functional dystrophin protein is due to a disruption of translation caused by nonsense or deletion mutations in the dystrophin gene, a large gene located at Xp21.2 (Muntoni et al., *Lancet Neurol.*, 2: 731-740, 2003). A strategy for correcting DMD consists in using antisense oligonucleotides (AON) to skip some exons and thus express a truncated, yet functional, form of the protein. This technique, designated exon skipping, uses oligonucleotides complementary to the sequences involved in the splicing of the exons to skip (Wood et al., *PLoS Genet.*, 3 (6): e109, 2007; Du & Gatti, *Curr Opin Mol Ther.*, 11(2):116-23, 2009). In particular, the present inventors have shown that it is possible to correct DMD by exon skipping in mouse by using a modified U7 snRNA redirected to the spliceosome by replacement of the endogenous sm-binding domain with the one of the U1 snRNA, the smOPT (WO 2006/021724; Goyenvalle et al., *Science*, 306: 1796-1799, 2004). However, this technique has not yet been adapted for use in human patients.

Another important dystrophy is myotonic dystrophy (*dystrophia myotonica*, DM), of which the type 1 (DM1, also known as Steinert's disease) is the most prevalent. DM1 is a dominant inherited disease, caused by expanded CTG repeats in the 3' untranslated region of the DM protein kinase (DMPK) gene (Gene map locus: 19q13.2-q13.3). The mutant DMPK mRNA is trapped in the nucleus and the CUG expansion alters binding of RNA-binding proteins to the molecule (Davis et al., *Proc. Natl. Acad. Sci. U.S.A.*, 94: 7388-7393, 1997). Such an accumulation alters the regulation of alternative splicing, which subsequently leads to mis-splicing of several pre-mRNA transcripts and neuromuscular dysfunction. Strategies for phenotype rescue in DM1 have been evaluated with the use of AON targeting CUG expansions in murine DM1 models (Wheeler et al., *Science*, 325: 336-339, 2009; Mulders et al., *Proc. Natl. Acad. Sci. U.S.A.*, 106: 13915-13920, 2009; Du & Gatti, *Curr Opin Mol Ther.*, 11(2): 116-23, 2009). However, the use of synthetic oligonucleotides requires repeated treatments. Indeed, there is currently no cure for or treatment specific to myotonic dystrophy.

Apart from the muscular dystrophies, another important muscular disease is Spinal Muscular Atrophy (SMA): it is the most common cause of genetically determined neonatal death. SMA is a hereditary neuromuscular disease characterized by degeneration of motor neurons, resulting in progressive muscular atrophy (wasting away) and weakness. The disorder is caused by an abnormal or missing gene known as the survival motor neuron gene, which is responsible for the production of the Survival Motor Protein (SMN), a protein essential to motor neurons. In humans, there are two copies of the SMN gene, named SMN1 and SMN2, and both mapped to the 5q12.2-q13.3 locus. Inactivation of the SMN1 gene leads to disease because the SMN2 gene cannot compensate for its absence. The reason for this is a critical C to U substitution in exon 7 of the SMN2 gene that does not change the codon but prevents its recognition by the splicing machinery. As a result of this substitution, the SMN2 gene predominantly (90% of the transcript) produces a transcript where exon 7 is skipped, leading to the production of a truncated protein and inability to compensate for SMN1 inactivation.

Current strategies for developing SMA therapeutics include identifying drugs that increase SMN2 levels, enhance residual SMN2 function, or otherwise compensate for the loss of SMN1 activity. Drugs such as butyrates, valproic acid, hydroxyurea, and riluzole (Rilutek®, Sanofi-Aventis) are or have been under clinical investigation for SMA. Although gene replacement strategies are being tested in animals (Foust et al., *Nat Biotechnol.*, 28(3): 271-4, 2010), current treatment for SMA consists of prevention and management of the secondary effect of chronic motor unit loss. There is currently no drug known to alter the course of SMA.

There is thus still a need for new treatments of neuromuscular diseases. In particular, the inventors have developed a new modified human U7 snRNA which comprises a smOPT domain and a sequence antisense to at least a part of the target pre-mRNA. They have shown that an interaction between the antisense moiety and the U7 loop is required to obtain active U7-derived snRNPs which can be used for treating neuromuscular diseases.

SUMMARY

The inventors have shown that a modified U7 snRNA comprising the smOPT sequence (U7smOPT) and an antisense sequence is useful for treating neuromuscular disease in particular by exon skipping, exon inclusion, or eradication of deleterious mRNAs. However, introducing the appropriate antisense sequences into U7smOPT is not as much as sufficient, and, in many cases, the subsequent engineered U7 does not interfere efficiently with the splicing machinery. Some antisense polynucleotides, even though they are designed to perfectly interact with a target pre-mRNA sequence, do not lead to correct splicing (see e.g. antisense SD23 or M23D in the experimental examples).

The inventors have now found that correct folding of the antisense-U7smOPT is required for efficiency. Without being bound by theory, one hypothesis to explain this phenomenon is that antisense sequences might impact the folding of the subsequent snRNP, eventually hampering its cellular trafficking and addressing to the spliceosome. An interaction by hybridization between the antisense part of the molecule and the U7 loop is thus essential for allowing the proper folding of the modified molecule. In addition, the inventors have found that, when no such interaction exists naturally, it is possible to engineer the antisense-U7-SmOPT molecule by adding to the said molecule a domain, the "kiss domain", capable of hybridizing with the stem loop.

DETAILED DESCRIPTION

According to a first aspect, the invention is directed to a modified U7 snRNA, wherein the Sm binding domain has been replaced by a smOPT sequence, and the antisense sequence by one or more other polynucleotides. In one embodiment, at least one other polynucleotide is an antisense of at least part of a target pre-messenger RNA (pre-mRNA). In another embodiment, at least one other polynucleotide (the kiss domain) is capable of hybridizing with the U7 loop. In yet another embodiment, at least one other polynucleotide is an antisense of at least part of a target pre-mRNA, and at least one other polynucleotide (the kiss domain) is capable of hybridizing with the U7 loop.

Thus, the invention provides a modified huU7 snRNA, comprising the following elements bound covalently from the 3' end to the 5' end:
 a polynucleotide having the sequence of SEQ ID NO. 1,
 a polynucleotide having the sequence of SEQ ID NO. 2, and
 one or more polynucleotides wherein
  at least one of the said polynucleotide is an antisense of at least part of a target pre-mRNA, and
  at least one of the said polynucleotides (the kiss domain) is capable of hybridizing with at least two nucleotides comprised within the nucleotides comprised between nucleotides 12 and nucleotides 20 of SEQ ID NO. 1.

Small nuclear ribonucleic acid (snRNA) is a class of small RNA molecules found within the nucleus of eukaryotic cells. They are involved in a variety of important processes such as RNA splicing (removal of introns from pre-mRNA), regulation of transcription factors (7SK RNA) or RNA polymerase II (B2 RNA), and maintaining the telomeres. They are always associated with specific proteins, and the resulting RNA-protein complexes are referred to as small nuclear ribonucleoproteins (snRNP) or sometimes as snurps. There are many snRNAs, which are denominated U1, U2 . . . U10.

The snRNA of the U7 type is normally involved in the maturation of histone mRNA. This snRNA has been identified in a great number of eukaryotic species (56 so far) and the U7 snRNA of each of these species should be regarded as equally convenient for this invention. Nevertheless, the use of the U7 snRNA of human origin is preferred. By "huU7 snRNA", it is herein meant a snRNA of human origin; the huU7 snRNA is also known as SU7 or Second U7 snRNA; for the purpose of this application, these denominations are interchangeable. In a preferred embodiment, the U7 snRNA is a single stranded polynucleotide having the sequence corresponding to Genbank entry number NR_023317.1.

Wild-type U7 snRNA includes a stem-loop structure, the U7-specific Sm sequence, and a sequence antisense to the 3' end of histone pre-mRNA.

By "modified snRNA", it is herein meant an RNA wherein the sequences involved in the initial function of the snRNA are inactivated. For example, it is known the snRNA molecules interact with a set of specific Sm proteins through a specific Sm-binding domain sequence to form snRNPs. In one embodiment, a modified snRNA is a snRNA wherein the Sm-binding domain has been replaced with the Sm-binding domain from another snRNA. In this embodiment, the function of the modified snRNA is altered by the change of Sm-binding domain. In particular, U7, a non-spliceosomal snRNA normally involved in the processing of the histone pre-mRNA 3' end, was redirected to the spliceosome by transforming the U7 Sm binding domain into the Sm binding consensus of U1 and U2, the two snRNAs that operate at the level of donor and acceptor splice sites, respectively (Gorman et al., *Proc Natl Acad Sci USA.*, 95(9): 4929-34, 1998). In a preferred embodiment, the sequence of the Sm-binding site has been modified in order to inactivate the histone pre-mRNA maturation while increasing the nuclear concentration of the U7 snRNA by replacing the natural Sm binding site with the SmOPT domain of sequence SEQ ID NO. 2.

In addition to the SmOPT domain, U7 comprises a sequence antisense to the 3' end of histone pre-mRNA. When this sequence is replaced by a sequence antisense to another target pre-mRNA, U7 is redirected to the new target pre-mRNA. Accordingly, the stable expression of modified U7 snRNAs containing the smOPT domain and an antisense sequence has resulted in sequence-specific modification of different targeted mRNA structures (Suter et al., *Hum Mol Genet.*, 8(13): 2415-23, 1999; Vacek et al., *Blood*, 101(1): 104-11, 2003). More recently, the inventors have shown high efficiency gene transfer into the skeletal muscle and complete dystrophin rescue after delivery of AAV-2/1 based vectors harboring an appropriately modified murine U7 gene along with its natural promoter and 3' elements (Goyenvalle et al., *Science*, 306: 1796-1799, 2004).

In one aspect, the modified U7 snRNA of the invention contains a polynucleotide which is an antisense to at least part of a target pre-mRNA. By antisense of at least part of target pre-mRNA, it is herein meant a polynucleotide which sequence is complementary to the sequence of the said part of the target pre-mRNA. This sequence can thus be an antisense directed towards the splicing site of at least one exon, i.e. it is capable of interfering with the splicing of the said exon. The antisense sequence is preferentially a sequence complementary to at last one sequence chosen in the group consisting of: 5' splice site (donor site); 3' splice site (acceptor site); intronic BP (Branching Point) sequence; and optionally internal purine-rich sequences, more specifically exon-internal splicing enhancer (ESE), and the intronic-splicing enhancer (ISE) sequences. In another embodiment, when exon inclusion is desired, the antisense sequence is preferentially a sequence complementary to an intronic silencer sequences (ISS) or to a terminal stem loop (TSL). In a further preferred embodiment, the target mRNA encodes a protein which function is altered in a neuromuscular disease. In a further more preferred embodiment, the said protein is dystrophin, DMPK, SMN1 or SMN2.

As used herein, "splicing" refers to the modification of a pre-mRNA following transcription, in which introns are removed and exons are joined. Splicing occurs in a series of reactions that are catalysed by a large RNA-protein complex composed of five snRNPs referred to as a spliceosome, within an intron, a 3' splice site, a 5' splice site, and a branch site are required for splicing. The RNA components of snRNPs interact with the intron and may be involved in catalysis. As used herein, the terms "intronic-splicing enhancer (ISE)", "intronic silencer sequences (ISS)", "terminal stem loop" and "exon-internal splicing enhancer (ESE)" refer to sequence elements within introns and exons, respectively, which control alternative splicing by the binding of trans-acting protein factors within a pre-mRNA thereby resulting in differential use of splice sites (see e.g. Buratti et al., *Nucleic Acids Res.*, 34(12):3494-510, 2006; Wang and Burge, *RNA*, 14: 802-813, 2008). By "exon skipping", it is herein meant the process of excluding an exon from the mature mRNA by modification of constitutive splicing. It includes the masking of key sequences involved in the splicing of targeted exons by using antisense sequences, such as the one contained within the modified U7 snRNA of the invention, that are complementary to exon definition sequences within a pre-mRNA As discussed above, exon splicing can be useful for restoring a near full-length, semi-functional dystrophin protein (Wood et al., *PLoS Genet.*, 3 (6): e109, 2007; Du & Gatti, *Curr Opin Mol Ther.*, 11(2):116-23, 2009); however, it can also be used for silencing a protein by excluding an exon without maintaining the reading frame. The term "exon inclusion", as used herein, relates to the process leading to the inclusion into the fully-processed mRNA of an exon which would have been otherwise left out of the mature mRNA because of a splicing defect. It normally involves masking an ISS and/or a TSL within the pre-mRNA using antisense sequences, such as the one contained within the modified U7 snRNA of the invention, which are complementary to the said ISS and/or TSL.

In another embodiment, at least part of a target pre-mRNA as detailed herein is a trinucleotide repeat expansion. In a further preferred embodiment, the trinucleotide repeat is CUG. In a yet further preferred embodiment, the antisense is comprises at least 15 repeats of the trinucleotide CAG. In another preferred embodiment, the target pre-mRNA encodes a protein which function is altered in neuromuscular dystrophy. In a further more preferred embodiment, the said protein is dystrophin or DMPK.

The inventors have found that it is not sufficient to replace the endogenous antisense sequence of the U7 snRNA with a sequence antisense to at least part of the target pre-mRNA. An interaction by hybridization between the antisense sequence and the U7 loop is required. By "U7 loop", it is herein meant the domain of the U7 snRNA wherein the bases are not paired. Preferentially, the U7 loop consists of the part of the U7 molecule comprised between nucleotides 12 and nucleotides 20 of SEQ ID NO. 1.

An efficient antisense sequence according to the invention is capable of hybridizing with the U7 loop. By "hybridization", it is herein meant the formation of hydrogen bonds between complementary bases. The interaction between the antisense and the U7 loop allows the correct folding of the modified U7 snRNA. The skilled person will have no difficulty realizing that, in order to ensure proper and stable folding, the hybridization between the antisense and the U7 loop requires a minimal strength, i.e. a minimal number of consecutive bases should be involved in the interaction. It is clear that the greater the number of bases involved in the antisense-U7 loop interaction, the stronger this interaction. Preferentially, the number of bases is at least 3; more preferentially, it is at least 4. In a yet further preferred embodiment, the bases of the U7 loop involved in the interaction are ACUU. In another further preferred embodiment, the bases of the U7 loop involved in the interaction are GCUUU.

The inventors have also found that it is possible to correct an inefficient antisense sequence by adding to the said antisense sequence a polynucleotide, the kiss domain, capable of hybridizing with the U7 loop. The said kiss domain comprises a number of nucleotides capable of hybridizing with the U7 loop. Preferentially, the kiss domain comprises at least 3 nucleotides; more preferentially, it comprises at least 4 nucleotides.

In a yet further preferred embodiment, the kiss domain has a sequence chosen between AAGU, GAGU, GGGU and AGGU. In another further preferred embodiment, the kiss domain has a sequence chosen between GCAGU, GAAGU, GCGGU, GGAGU, GAGGU and GGGGU.

The invention is also directed to a polynucleotide comprising a gene encoding a modified U7 snRNA as described above. A gene according to the invention is any nucleic acid molecule encoding a biological product, i.e. a RNA, protein, polypeptide or peptide. A gene, within the context of the instant invention, therefore includes gDNA, cDNA or synthetic or semi-synthetic DNAs. In particular, genes according to the instant invention can be any nucleic acid encoding a biological product, comprising one or more naturally present or artificially produced untranslated region(s). It is most useful when the gene is not limited to the sequences directly encoding the modified U7 snRNA of the invention but is under the control of the regulatory elements required for its expression. Therefore, the invention encompasses a gene comprising the modified U7 described above, said gene being fused to regulatory sequences. A lot of strong, constitutive promoters are known to the person skilled in the art. For example, the skilled person may use any of the promoters of human housekeeping genes listed in Eisenberg et al. (*Trends in Genetics* 19: 362-365, 2003). However, in order to ensure proper expression of the modified U7 snRNA of the invention, it is more advantageous to use the endogenous U7 promoter. Even more advantageously, the promoter is the human U7 promoter. In a very preferred embodiment, the promoter is the human U7 promoter having the sequence SEQ ID NO. 3.

In order to obtain effective therapeutic RNA molecules in vivo, several important parameters were considered. Not only must the genes for these RNAs be cloned under efficient promoters producing high levels of expression but, in addition, the RNA context in which the therapeutic RNA is embedded should provide stability and specific subcellular localization. Moreover, downstream sequences should help define the correct transcription termination site of the modified U7 snRNA of the invention. Therefore, the gene of the invention also includes the 3' regulatory sequences of the endogenous U7 gene. When the U7 gene used is the human gene, it is advantageous to use the downstream sequences of the said human gene. In particular, it is most advantageous to use the 230 nucleotides of the downstream sequences of the said human gene represented by the sequence SEQ ID NO: 4.

The invention provides vectors comprising the polynucleotides of the invention. In one embodiment, the vector contains a polynucleotide comprising the gene encoding the modified U7 snRNA. This gene may be advantageously cloned under the control of appropriate promoter sequences, as detailed above. In addition, it is beneficial to insert in the vector of the invention the proper 3' sequences downstream of the modified U7 snRNA gene. In order to ensure that en exon is skipped, it may be useful to use in the same vector two modified U7 snRNAs with antisense sequences for distinct targets, preferentially the 5' donor site and the BP sequence. Antisense sequences directed against splice sites of at least two distinct exons may also be associated in the same vector. Alternatively, it is possible to use several constructs, each carrying a distinct antisense sequence, the said sequences being directed towards one or several exons. Practically, when several antisense sequences (directed towards the same exon or several distinct exons or against an exon and an intron) are associated, the following cases can be encountered:

the antisense sequences are inserted within the same modified U7 snRNA, the said snRNA being carried by a unique vector, or the antisense sequences are inserted in different U7 snRNA, each snRNA being carried by a vector.

The vector of the invention may be either derived from a virus or from a non-viral origin.

Non-viral vectors include plasmids. Such a plasmid may be a conditionally replicating plasmid that is incapable of replicating in the patients for safety reasons. These plasmids may be based on the plasmids described in the patent PCT applications WO 97/10343 and WO 2009/027351. Naked plasmid DNA can be directly injected into muscle cells (Wolff et al, *Science*, 247: 1465-1468, 1990) or attached to gold particles that are bombarded into the tissue (Cheng et al, *Proc. Natl. Acad. Sci. U.S.A.*, 90: 4455-4459, 1993). Though not very efficient, this can result in prolonged low level expression in vivo. The plasmid DNA can also be transfected into the cell with the use of non-viral gene delivery vectors, termed "self-assembled" systems, based on cationic molecules, which form spontaneous complexes with negatively charged nucleic acids (Eliyahu et al., *Molecules*, 10: 34-64, 2005).

In a preferred aspect of the invention, the vector is a viral vector. By replacing genes that are needed for the replication phase of the virus life cycle (the non-essential genes) with foreign genes of interest, the recombinant viral vectors can transduce the cell type it would normally infect. To produce such recombinant viral vectors the non-essential genes are provided in trans, either integrated into the genome of the packaging cell line or on a plasmid. Several vectors based on viruses such as adenovirus, adeno-associated virus (AAV), lentivirus, or herpes simplex virus 1 (HSV1), are available for gene therapy. All of them are encompassed within this invention.

Adenoviral vectors are currently the most frequently used viral vectors in gene therapy in humans. The use of so-called third-generation (or "gutless") adenoviral vectors (Lindermann and Schnittler, *Thromb. Haemost.*, 102: 1135-1143, 2009) is preferred for the use in the present invention. Said vectors need not be detailed here, since the skilled person is fully aware of the characteristics and uses of said adenoviral vectors.

Alternatively the skilled person may use a lentiviral vector to deliver the modified U7 snRNA of the invention. Preferentially, the said lentiviral is a self-inactivating (SIN) lentivirus. Nevertheless, any lentiviral vector can be used in the context of the present invention. The construction and the manipulation of lentiviral vectors are well known to the skilled person.

The preferred viral vectors according to the invention are based on adenoviral-associated virus or AAV. Amongst the 8 serotypes, the AAV used for treating a neuromuscular disease according to the invention is preferentially an AAV1, i.e. its capside is of the serotype 1. AAV1 has been shown to be the most efficient for muscle cells transduction. On the other hand, the sequences of a viral origin, and in particular the ITRs, associated to the transgene are preferably of AAV2 origin. The resulting AAV-based vector of the invention has, preferentially, a 2/1 pseudotype. The skilled person will easily realize, however, that the invention is not restricted to this particular vector; in fact, all AAV serotypes are equally suited for use in this invention. For example, AAV6, AAV8 or AAV9 also effectively transduce striated muscle cells, while AAV5 is highly efficient in transducing neural cells in the brain (Markakis et al., *Molecular Therapy*, 18: 588-593, 2010); all of them can therefore be used successfully in the context of the invention. Like adenoviral and lentiviral vectors, the AAV-based vectors have already been used extensively by the skilled person for gene therapy purposes (see e.g. Michelfelder and Trepel, *Adv Genet.*, 67: 29-60, 2009); there is thus no need for detailing methods for constructing and using the said AAV vectors.

The vectors according to the invention can also be used in in vitro and/or ex vivo applications. Although the vectors of the invention are preferentially used by direct injection in the target muscle, or by systemic intra-venous, intra-arterial delivery or delivery into the brain or the cerebro-spinal fluid, they can also be used to test the efficiency of potential antisense sequences in vitro, directly in differentiated muscle cells, e.g. taken from the patient. Moreover, if these vectors are introduced by transfection into a cell capable of muscle differentiation, e.g. a myoblast or another myogenic stem cell such as a $CD133^+$ cell (Torrente et al., *Cell Transplant.*, 16(6):563-77, 2007), a $SMALD^+$ cell (Vauchez et al., *Mol Ther.* 17(11):1948-58, 2009), a mesangioblast, or a pericyte, all of which are precursors of the muscle cells, the said transfected cell can then be transplanted into the patient. It is even possible to use human cells which have transformed into pluripotent stem cells or iPS by the methods of the art (see e.g. Takahashi et al., *Cell*, 131: 861-872, 2007; Yamanaka, *Cell Stem Cell.*, 1(1):39-49, 2007; Park et al., *Nature*, 451(7175): 141-6, 2008; Park et al., *Nat Protoc.*, 3(7):1180-6, 2008; EP 2 096 169; WO 2008/118820; US2008/0280362). Said iPS can thus be transfected by the vectors of the invention and transplanted into the patient.

The invention thus also encompasses an isolated eukaryotic cell transfected by the vectors of the invention. The said cells are preferentially a blood-derived or skeletal muscle-derived myogenic cell, a myoblast or a cell capable of muscle differentiation. In a specific embodiment of the invention, the cell is capable of muscle differentiation is an induced pluripotent stem cell.

The invention also relates to a therapeutic composition for the treatment of a neuromuscular disease which comprises a therapeutically effective amount of a vector of the invention and a pharmaceutically acceptable carrier. In another aspect, instead of the vector, the pharmaceutical composition of the invention contains an effective amount of a cell transfected by the vector of the invention as described above, as well as a pharmaceutically acceptable carrier. In one embodiment, said pharmaceutical composition is for the treatment of a neuromuscular disease, including (but not limited to) the following diseases: Duchenne (DMD), Becker, limb girdle, congenital, facioscapulohumeral, myotonic (and in particular DM1), oculopharyngeal, distal, Emery-Dreifuss, and SMA. More preferentially, the therapeutic compositions of the invention are used to treat DMD, DM1 or SMA.

The instant invention provides pharmaceutical compositions comprising:

a) an effective amount of vector or transfected cell of the present invention, and;

b) a pharmaceutically acceptable carrier, which may be inert or physiologically active.

As used herein, "pharmaceutically-acceptable carriers" includes any and all solvents, dispersion media, coatings, antibacterial and antifungal agents, and the like that are physiologically compatible. Examples of suitable carriers, diluents and/or excipients include one or more of water, saline, phosphate buffered saline, dextrose, glycerol, ethanol, and the like, as well as combination thereof. In many cases, it will be preferable to include isotonic agents, such as sugars, polyalcohols, or sodium chloride in the composition. In particular, relevant examples of suitable carrier include: (1) Dulbecco's phosphate buffered saline, pH~7.4, containing or not containing about 1 mg/ml to 25 mg/ml human serum albumin, (2) 0.9% saline (0.9% w/v sodium chloride (NaCl)), and (3) 5% (w/v) dextrose; and may also contain an antioxidant such as tryptamine and a stabilizing agent such as Tween 20. When the vector of the invention is intended to treat SMA, it is possible to use mannitol as a carrier, since mannitol is a well known blood-brain barrier interruptive (Fu et al., *Molecular Therapy*, 8: 911-917, 2003).

The compositions herein may also contain a further therapeutic agent, as necessary for the particular disorder being treated. For example, the said composition may contain, in addition to a vector carrying the gene for a modified U7 snRNA, a second vector comprising another modified U7 snRNA gene. Said modified U7 genes may contain antisenses directed to the same exon or to different exons, or to an exon and an intron, as described above.

The compositions of the invention may be in a variety of forms. These include for example liquid, semi-solid, and solid dosage forms, but the preferred form depends on the intended mode of administration and therapeutic application. Administration of the composition according to the present invention to attain the therapeutic objectives may be by local, intramuscular, loco-regional, parenteral, intravenous, intra-arterial, intramyocardial, pericardial, epicardial or via intracoronary administration to the target cardiac muscle tissue, or by intra-cerebral administration or by administration into the cerebro-spinal fluid. Preferably, intramyocardial, epicardial, pericardial or intracoronary administration is conducted using a needle or a catheter. Typical preferred compositions are in the form of injectable or infusible solutions.

According to one embodiment of the present invention, the vector of the invention is administered in a localized manner to the target dystrophic muscle tissue. In another embodiment, the vector of the invention is administered intra-cerebrally or into the cerebro-spinal fluid. The site of the administration will depend upon the pathology the vector of the invention is intended to treat: it is clear that administration to the muscle will be most effective for neuromuscular dystrophies, while administration to the brain or the cerebro-spinal fluid will be particularly helpful for SMA. While any suitable means of administering the vector to the target tissue can be used within the context of the present invention, preferably, such a localized injection to the target muscle tissue, the brain, or the cerebro-spinal fluid is accomplished by directly injecting the vector to the muscle, the brain, or the cerebro-spinal fluid using a needle. By the term <<injecting", it is meant that the vector is forcefully introduced into the target tissue. Any suitable injection device can be used according to the present invention.

When the vector of the invention is injected directly into the dystrophic muscles or into the brain or into the cerebro-spinal fluid, the pharmaceutical compositions are preferably in a liquid form. Sterile compositions for injection can be prepared by incorporating the vector of the present invention in the required amount in the appropriate solvent, followed by sterilization by microfiltration. As solvent or vehicle, there may be used water, saline, phosphate buffered saline, dextrose, glycerol, ethanol, and the like, as well as combination thereof. In many cases, it will be preferable to include isotonic agents, such as sugars, polyalcohols, or sodium chloride in the composition. These compositions may also contain adjuvants, in particular wetting, isotonizing, emulsifying, dispersing and stabilizing agents. Sterile compositions for injection may also be prepared in the form of sterile solid compositions which may be dissolved at the time of use in sterile water or any other injectable sterile medium.

Dosage levels of the order of from about 0.1 mg to about 140 mg per kilogram of body weight per day are useful in the treatment of the above-indicated conditions (about 0.5 mg to about 7 g per patient per day). While the effective dose will vary depending on the weight and condition of a given subject suffering from neuromuscular disease, it is considered within the skill in the art to determine the appropriate dosage for a given subject and conditions.

The modified U7 snRNA of the invention are useful for restoring the normal function of a cellular protein. More specifically, the modified U7 snRNA of the invention can promote exon skipping, exon inclusion, or eradication of deleterious mRNAs, such that the resulting cellular protein is now fully or at least partially functional. Thus, the invention also relates to a method for restoring the function of a cellular protein by exon skipping, exon inclusion, or eradication of deleterious mRNAs, comprising the step of contacting a cell with the vector of the invention. The use of the modified U7 snRNA of the invention is thus not restricted to a specific type of pathology, but can be applied for treating any disease resulting from a splicing defect. Nevertheless, in the context of the present application, the said cellular protein is preferentially a protein which function is altered in a neuromuscular disease. Even more preferentially, the said cellular protein is dystrophin, DMPK or SMN.

The invention thus also provides a method for treating a muscular disease by administering an affective dose of any of the vectors of the invention, preferably in a pharmaceutical composition as described hereabove. The invention thus also relates to the use of the vectors of the invention as a medicament. More specifically, the vectors of the invention are used as medicament for treating a neuromuscular disease, including (but not limited to) the following diseases: Duchenne (DMD), Becker, limb girdle, congenital, facioscapulohumeral, myotonic (and in particular DM1), oculopharyngeal, distal, Emery-Dreifuss, and SMA. More preferentially, the vectors of the invention are used to treat DMD, DM1 or SMA.

The present invention also includes kits, e.g., comprising one or more described vectors and instructions for the use of the said vector for treating neuromuscular diseases. The instructions may include directions for using the vectors in vitro, in vivo or ex vivo. Typically, the kit will have a compartment containing the vectors. The vectors may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the vectors prior to administering to a patient, and tools that aid in administering the vectors to a patient.

BRIEF DESCRIPTION OF THE DRAWINGS

FIG. 3 Sequence of the modified human U7 gene containing its natural promoter, the CAG$_{15}$ antisense sequence (in red), the Sm binding domain (Sm-Opt in blue), the loop (in green) and its 3' downstream elements.

FIG. 10 Dystrophin rescue in transversal sections of injected TA muscles with various constructs targeting key motives involved in definition of exon 23 (SD: splice donor—BP22: branch point intron 22).

EXPERIMENTAL EXAMPLES

Figure 1:
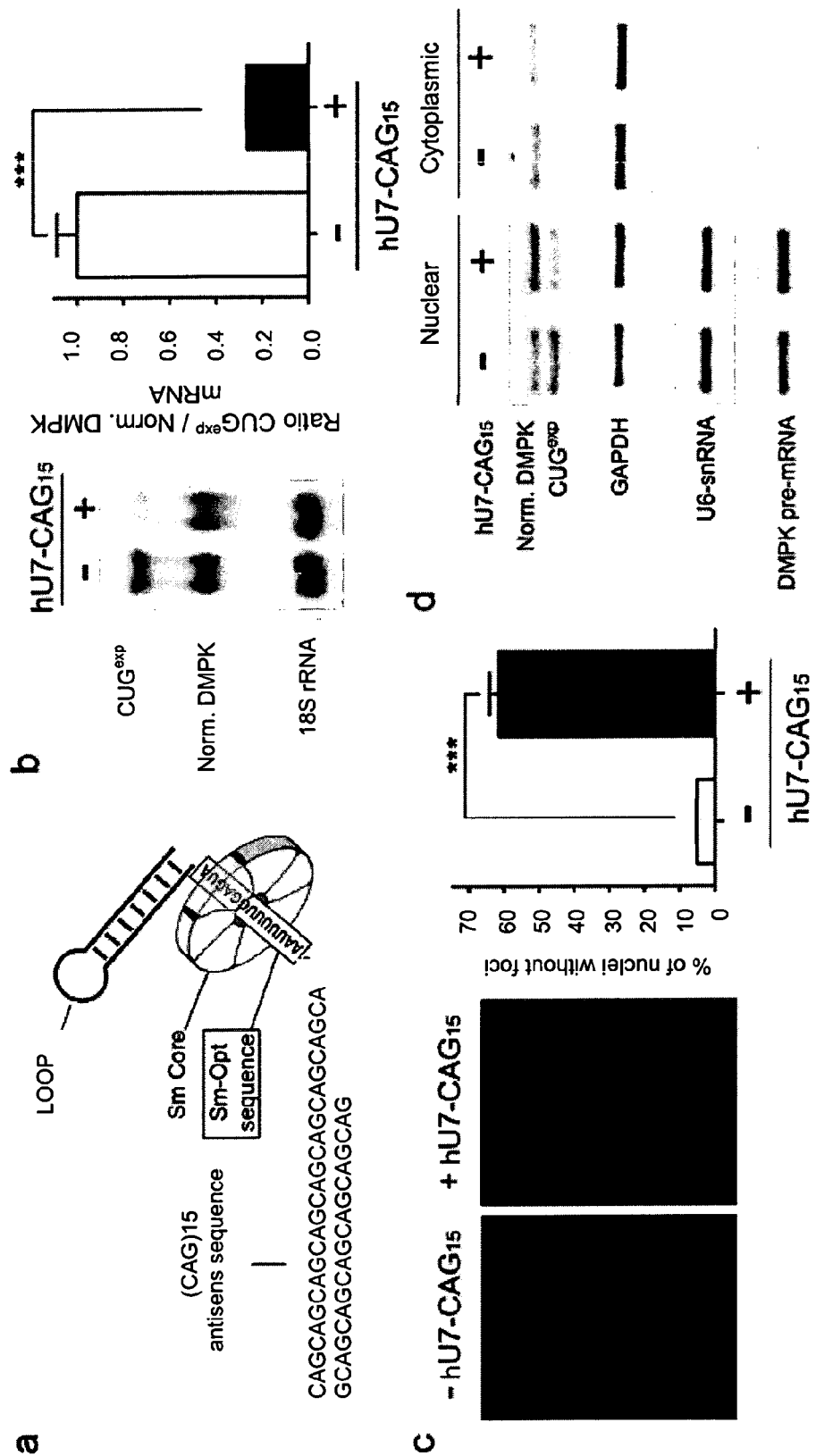
FIG. 1 $CUG^{exp}$-mRNAs silencing by $hU7$-$CAG_{15}$. (*a*) Structure of the $hU7$-snRNA-$CAG_{15}$ ($hU7$-$CAG_{15}$) indicating the loop, the Sm-Opt and the CAG antisense sequences. (*b*) Representative northern blot and analysis (n=5) of DMPK mRNA expression in DM1 muscles cells (13/800 CTG) transduced with hU7-CAG$_{15}$ lentiviral vector (4-8×106 vg/mL). (c) FISH analysis (n=4) of the number of CUG$^{exp}$-mRNA foci (red spots) into the nuclei (blue) of hU7-CAG$_{15}$ transduced DM1 cells (800 CTG). (d) RT-PCR assay of normal and CUG$^{exp}$ DMPK, U6snRNA mRNAs and DMPK pre-RNAs in nuclear and cytoplasmic fractions of DM1 converted muscle cells (1300 CTG). BpmI restriction site polymorphism located within exon 10 of expanded DMPK allele allows distinguishing normal and CUG$^{exp}$ allele products.

Selective Destruction of Mutated mRNAs in DM1 by Using Modified HU7-snRNAs

Materials and Methods
Cell Culture

Human muscle cells were isolated from skeletal muscle biopsies or autopsies as described (Edom et al., *Dev Biol*, 164: 219-229, 1994), in accordance with French legislation on ethical rules. Wild-type (WT) and DM1 myoblasts were grown in HAM's F10 medium supplemented with 20% FCS and 5 µg/mL gentamycin (Invitrogen), at 5% CO2 and 37° C. To trigger differentiation, growth medium was removed from subconfluent cultures and replaced by DMEM medium supplemented with 10 µg/mL insulin and 100 µg/mL transferring (Sigma). DM1 fibroblasts containing a BpmI polymorphic restriction site on the expanded DMPK allele (Hamshere et al., *Proc Natl Acad Sci USA*, 94: 7394-7399, 1997) were immortalized and converted into muscle cells using an inducible Mood system as previously described (Chaouch et al., *Hum Gene Ther*, 20: 784-790, 2009).

Lentivirus Production and Transduction

A self-inactivated HIV-1-based lentivirus vector, pRRL-hU7-CAG$_n$ was generated from the previously described pRRL-cPPT-hPGK-EGFP-WPRE vector (Follenzi et al., *Nat Genet*, 25: 217-222, 2000). VSV-G-pseudotyped vectors were produced by transient transfection of 293T cells (Charrier et al., *Gene Ther*, 12: 597-606, 2005). The conditioned medium containing virus particles was collected and concentrated by ultracentrifugation. Vector titers (vector genome vg/mL) were determined by quantitative PCR on genomic DNA of infected cells as described (Charrier et al., *Gene Ther*, 12: 597-606, 2005). 1×10$^6$ to 1×10$^7$ vg/mL were used to transduce 1.5×10$^5$ human muscle cells. Vector transduction was performed overnight in the presence of 4 µg/ml of polybrene (Sigma) and the transduced cells were grown and amplified at least one week before analyses.

RNA Isolation and Northern Blot

Cells were lyzed in a proteinase K buffer (500 mM NaCl, 10 mM Tris-HCl, pH 7.2, 1.5 mM MgCl$_2$, 10 mM EDTA, 2% SDS and 0.5 mg/mL of proteinase K) for 45 min at 55° C. Then, RNA were isolated using TRIzol reagent (Invitrogen) according to the manufacturer's protocol. RNA were also isolated from nuclear and cytoplasmic fractions prepared as described previously (Hamshere et al., *Proc Natl Acad Sci USA*, 94: 7394-7399, 1997) by hypotonic lysis in the presence of NP-40. For Northern blot analysis, 8-10 µg of RNA was separated on 1.3% agarose MOPS-gels containing 0.66 M formaldehyde and transferred onto Hybond-N$^+$ membrane (Amersham Pharmacia Biotech) by capillary transfer with 10×SSC. Blots were hybridized with random-primed $^{32}$P-labeled (Bgl II-SacI fragment of DMPK cDNA) probe in a hybridization buffer (2% SDS, 10% dextran sulfate, 1×SSPE, 10 µg/ml salmon sperm DNA, 2% Denhart's) at 68° C. overnight. Signals were analyzed on a phospho-imager (Molecular Imager FX, Bio-Rad) and quantified using Quantity One (Bio-Rad). All values were normalized to 18S rRNA signal after hybridization with 5'-end $^{32}$P-labeled 18S rRNA-oligonucleotide probes.

RT-PCR Analysis

One µg of RNA was reverse-transcribed into cDNA according to the manufacturer's protocol (Invitrogen) in a total volume of 20 µL. One µL of cDNA preparation was subsequently used in a semiquantitative PCR analysis according to standard procedures (ReddyMix, Thermo Scientific). PCR amplification was carried out for 20-35 cycles, within the linear range of amplification for each gene. The signal of GAPDH was used for normalization. PCR products were analyzed on 1-3% agarose gels, stained by ethidium bromide. Quantification was done using the Quantity One software (Bio-Rad). For alternative splicing analysis, the genes and exons selected were previously described as altered in muscle from DM1 patients: exon 78 for DMD (dystrophin) (Nakamori et al., *Muscle Nerve*, 36: 251-257, 2007), exon 7 for LDB3 (cypher) (Lin et al., *Hum Mol Genet*, 15: 2087-2097, 2006) and exon 11 for BIN1 (bridging integrator1) (Hammer et al., submitted). The ratios of exon inclusion were quantified and expressed as percentage of inclusion relative to total intensities of isoforms signals. For DMPK analysis, to distinguish the two alleles of DMPK, 6 μL of the PCR mixture was put into a 25-μl digestion mixture containing 2.5 units of BpmI (New England Biolabs) and incubated overnight at 37° C. as described (Hamshere et al., *Proc Natl Acad Sci USA*, 94: 7394-7399, 1997).

The following primers were used:

```
GAPDH-F,
                                     (SEQ ID NO: 5)
TGAAGGTCGGAGTCAACGGATTTGGT

GAPDH-R,
                                     (SEQ ID NO: 6)
GATGACAAGCTTCCCGTTCTCAGCC

U6snRNA-F,
                                     (SEQ ID NO: 7)
CTCGCTTCGGCAGCACA

U6snRNA-R,
                                     (SEQ ID NO: 8)
AACGCTTCACGAATTTGCGT

DMPK exon 9-exon 10-F,
                                     (SEQ ID NO: 9)
CACTGTCGGACATTCGGGAAGGTGC DMPK exon 9-exon 10-R,
                                     (SEQ ID NO: 10)
GCTTGCACGTGTGGCTCAAGCAGCTG DMPK intron 9-intron 10-F,
                                     (SEQ ID NO: 11)
CTACCCACAGGCCAGAAGTT DMPK intron 9-intron 10-R,
                                     (SEQ ID NO: 12)
GGAAGCCCTCACCTTTTCTC DMPK splice junction exon 14/16-exon 16-F,
                                     (SEQ ID NO: 13)
CTGCTCCCTGCCAGGGCTGA DMPK splice junction exon 14/16-exon 16-R,
                                     (SEQ ID NO: 14)
TGTCGGGGTCTCAGTGCATCCA CPA6-F,
                                     (SEQ ID NO: 15)
ACTGATGTCCATATCCCCCA CPA6-R,
                                     (SEQ ID NO: 16)
TTTGAGTCGTGATCGTCTGC LTBP3-F,
                                     (SEQ ID NO: 17)
GAGAAGAGCCTGTGTTTCCG LTBP3-R,
                                     (SEQ ID NO: 18)
GAAAAGTCACTCTCGCCCTG LRP8-F,
                                     (SEQ ID NO: 19)
CTCCACTGACTTCCTGAGCC LRP8-R,
                                     (SEQ ID NO: 20)
GTGCTCGGTAGCACCTCTTC TMCC1-F,
                                     (SEQ ID NO: 21)
GAGCAAAGGTGACTGGCTTC TMCC1-R,
                                     (SEQ ID NO: 22)
CGCTCCTCCTGTAAGGTCTG CASK-F,
                                     (SEQ ID NO: 23)
CAGAGTTCGGCTGGTACAGT CASK-R,
                                     (SEQ ID NO: 24)
ACAGGACGAAGACTGAGTGC MAP3K4-F,
                                     (SEQ ID NO: 25)
AAGGGCACGTATAGCATTGG MAP3K4-R,
                                     (SEQ ID NO: 26)
TGGTTCTCCAGCAGGTCTCT BIN1-exon 11-F,
                                     (SEQ ID NO: 27)
AGAACCTCAATGATGTGCTGG BIN1-exon 11-R,
                                     (SEQ ID NO: 28)
TCGTGGTTGACTCTGATCTCGG DMD-exon 78-F,
                                     (SEQ ID NO: 29)
TTAGAGGAGGTGATGGAGCA DMD-exon 78-R,
                                     (SEQ ID NO: 30)
GATACTAAGGACTCCATCGC LDB3-exon 7-F,
                                     (SEQ ID NO: 31)
GCAAGACCCTGATGAAGAAGCTC LDB3-exon 7-R,
                                     (SEQ ID NO: 32)
GACAGAAGGCCGGATGCTG
```

FISH and Immunofluorescence

Fluorescent in situ hybridization (FISH) was done as described (Taneja, *Biotechniques*, 24: 472-476, 1998) using a Cy3-labeled peptide nucleic acid $(CAG)_7$ probe. To determine the number of foci per nucleus, more than 500 DM1 cells were counted at least in three independent experiments. Combined FISHimmunofluorescence (IF) experiment was done as described (Klein et al., *Exp Cell Res*, 314: 1652-1666, 2008) using a monoclonal MBNL1 antibody (MB1a developed by G. Morris [Holt et al., *Am J Pathol*, 174: 216-227, 2009]) followed by a secondary Alexa 488-conjugated goat anti-mouse (Invitrogen) antibody. Pictures were captured using Leica confocal microscope and software (Leica microsystems), and processed with Adobe Photoshop software (Adobe System Inc.). For fusion index analysis, IF was performed on differentiated muscle cell cultures as described (Jacquemin et al., *J Cell Sci*, 120: 670-681, 2007) using a desmin (D33, DAKO) antibody and the nuclei were counterstained with Hoechst 33258 (Sigma). More than 1500 nuclei were counted and the fusion index was determined by the number of nuclei in differentiated myotubes (>2 myonuclei) as a percentage of the total number of nuclei in desmin-positive cells.

Western Blotting

Western blotting was performed with standard methods using a DMPK antibody (MANDM1) as described previously (Furling et al., *Am J Pathol*, 162: 1001-1009, 2003).

Statistical Analyses

Group data are expressed as mean+/−SEM. Between group comparison was performed by unpaired Student's t test (FIGS. 1*b*, 1*c*, 5 and 6) and Newman-Keuls test (FIG. 2*a*, 2*b*, 2*c*) using GraphPad Prism 4 software. Differences between groups were considered significant when $P<0.05$ (*, $P<0.05$; , $P<0.01$; *, $P<0.001$).

Results

We describe a novel function for modified hU7-snRNAs distinct from the block of pre-mRNA splicing events. hU7-snRNAs harboring a poly CAG sequence targeting the expanded $(CUG)_n$ tract in the 3' region of the DMPK transcripts caused specific nuclear degradation of mutant DMPK mRNAs without affecting wild-type allele products. Abolition of the RNA-gain-of-function toxicity responsible for myotonic dystrophy supports use of hU7-snRNA for gene silencing in non-coding repeat expansions disorders.

Myotonic dystrophy type 1 (DM1) is the most common neuromuscular dystrophy in adult (Harper. Myotonic dystrophy Third Edn., W.B. Saunder, London., 2001). It is a dominant inherited disease, which belongs to a group of RNA gain-of-function disorders (Shin et al., *M.S. Neurosci Lett*, 466: 99-102, 2009), due to expanded CTG repeats in the 3' untranslated region of the DM protein kinase (DMPK) gene (Brook et al., Cell, 68, 799, 1992). Mutant DMPK transcripts containing up to thousands of expanded CUG repeats ($CUG^{exp}$) are entrapped into the nucleus (Davis et al., *Proc Natl Acad Sci USA*, 94: 7388-7393, 1997). Such an accumulation alters the regulation of alternative splicing, which subsequently leads to mis-splicing of several mRNA transcripts and neuromuscular dysfunction (Ranum et al., *Annu Rev Neurosci*: 29, 259-277, 2006). Indeed, $CUG^{exp}$-DMPK mRNAs are folded in a way they bind RNA binding proteins to form stable ribonucleoprotein complexes or foci (Miller et al., *EMBO J*, 19: 4439-4448, 2000). These complexes sequester predominantly muscleblind-like 1 (MBNL1) proteins, ensuing a loss-of-function of this essential mRNA splicing regulator (Lin et al., *Hum Mol Genet*, 15: 2087-2097: 2006).

Strategies for phenotype rescue in DM1 have been evaluated with the use of synthetic antisense oligonucleotides targeting CUG expansions in murine DM1 models (Wheeler et al., *Science*, 325: 336-339, 2009; Mulders et al., *Proc. Natl. Acad. Sci. U.S.A.*, 106: 13915-13920, 2009). These studies have used local delivery of either morpholinos or 2'-O-methyl phosphorothioate oligonucleotides, with the aim to interfere and unfold $CUG^{exp}$-mRNAs to release MBNL1 from foci, then making it available for its overall splicing function. However, the use of synthetic oligos requires repeated treatments. To overcome this problem, we have designed an optimized human hU7-snRNA harboring the CAG antisense sequences to guarantee efficient long lasting effect. A fragment of about 0.5 kb containing the human U7 gene was amplified from human genomic DNA. The hU7-snRNA transcript was optimized as previously described (Goyenvalle et al., *Science*, 306: 1796-1799, 2004). First, its Sm binding domain was replaced by a canonical Sm sequence derived from the U2-snRNA (Sm-Opt) to bind appropriate Sm proteins that allow efficient snRNP assembly and increase its nuclear accumulation (Stefanovic et al., *Nucleic Acids Res*, 23: 3141-3151, 1995). Subsequently, the natural histone pre-mRNA complementary sequence of hU7-snRNA was replaced by a poly-CAG (FIG. 1a). The engineered hU7-snRNA-$CAG_n$ (hU7-$CAG_n$) was kept under the control of its natural promoter and 3' downstream elements (FIG. 3). Then, this construct was cloned into a lentiviral backbone for high efficiency gene transfer into human skeletal muscle cells.

Figure 4:
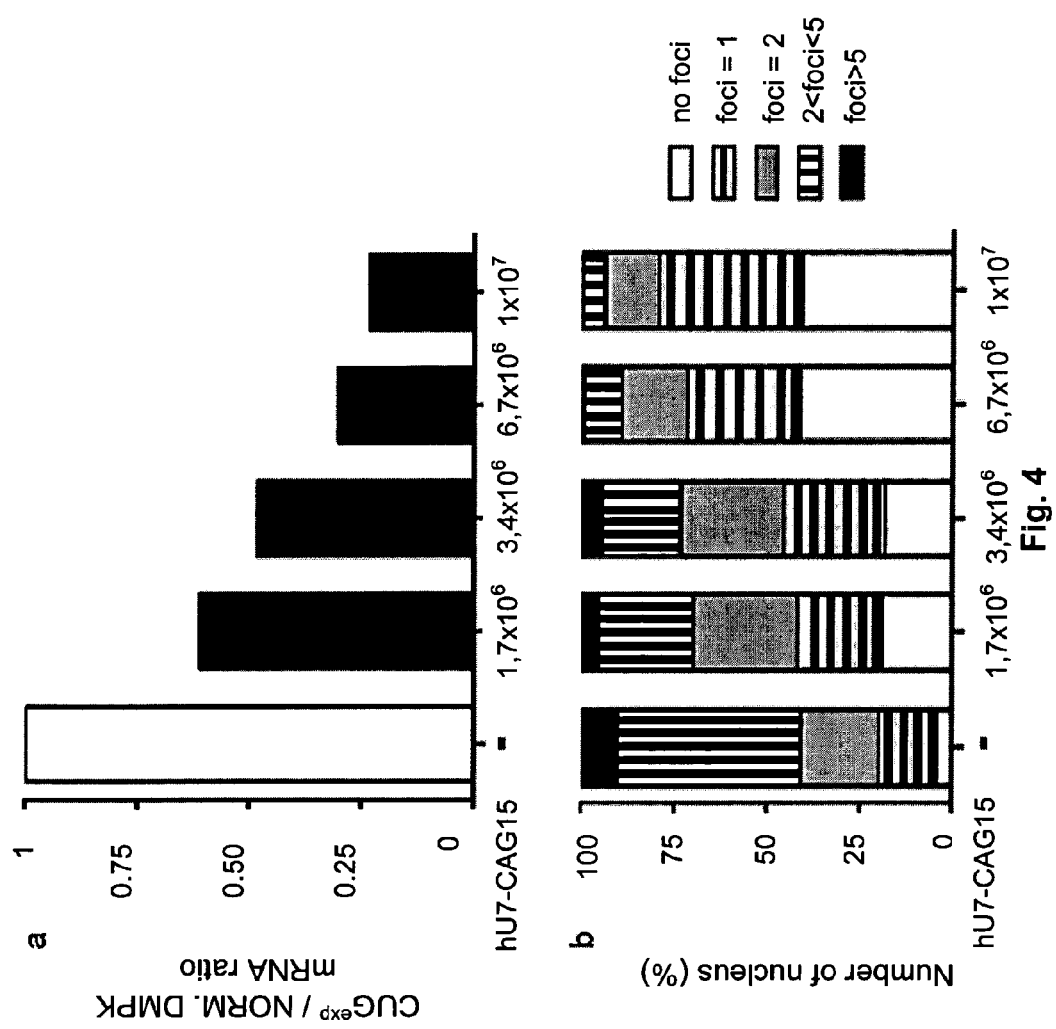
FIG. 4 (a) DMPK mRNA expression was analyzed in DM1 muscles cells (800 CTG) transduced with increasing concentration of hU7-CAG$_{15}$ lentiviral vector. (b) The repartition of CUG$^{exp}$-mRNA foci was determined in the nuclei of DM1 cells (800 CTG) transduced with increasing concentration of hU7-CAG$_{15}$ lentiviral vector.
Figures 5, 6:
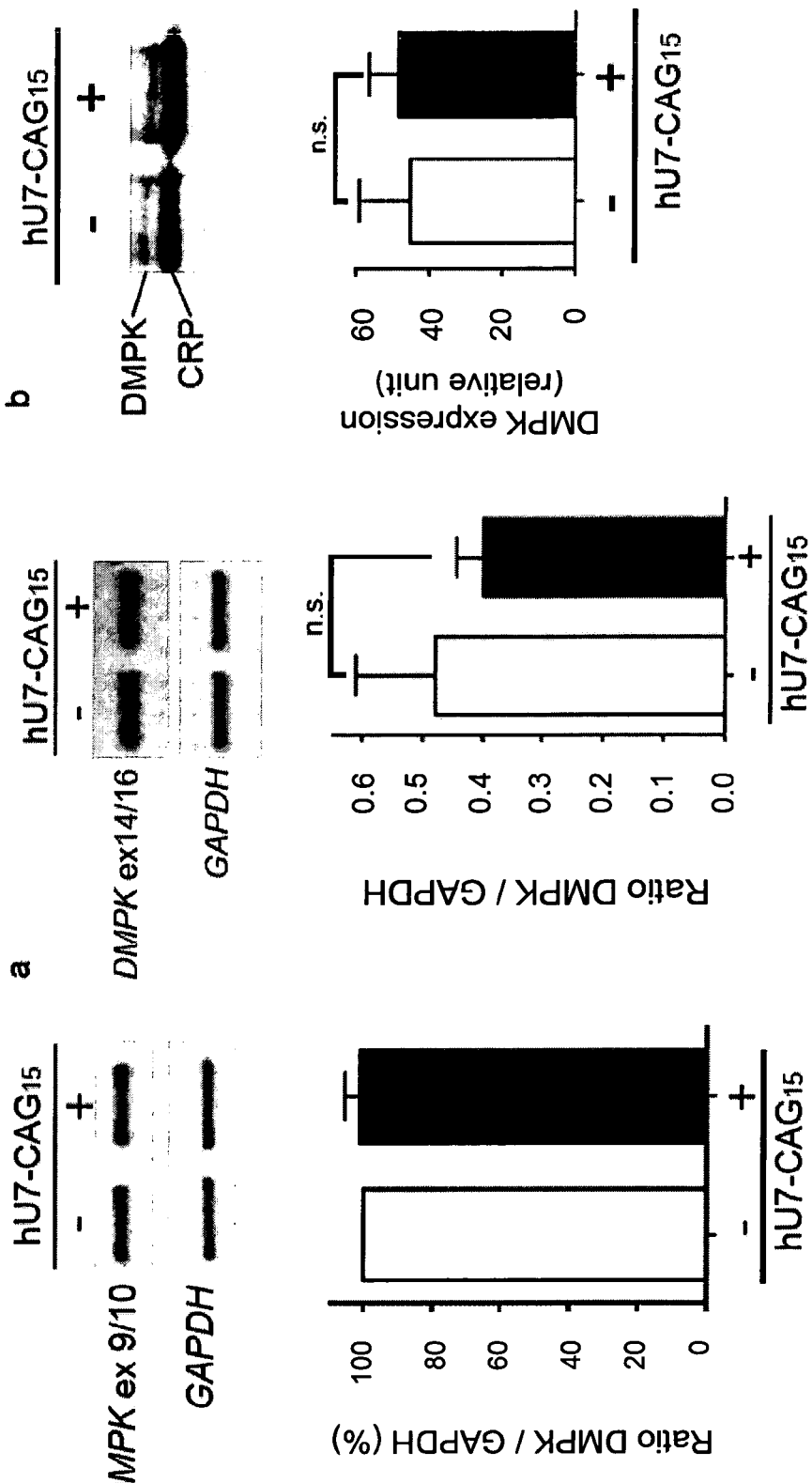
FIG. 5 DMPK mRNA expression in wild-type myoblasts (13/18 CTG) expressing hU7-CAG$_{15}$ was analyzed by RT-PCR (exon 9-exon 10). GAPDH mRNA was used as loading control (n=4).
FIG. 6 (a) Expression of the spliced DMPK mRNA isoform E14/16 (lacking exon 15 as well as CUG tract) in DM1 cells (800 CTG) was analyzed by RT-PCR with GADPH mRNA as loading control (n=3). (b) DMPK protein levels in DM1 cells were examined by Western blot using the MANDM1 antibody that detects DMPK but also CRP proteins (n=7). The level of CRP was not altered in DM1 cells and thus used as internal control of equal loading.
Figure 7:
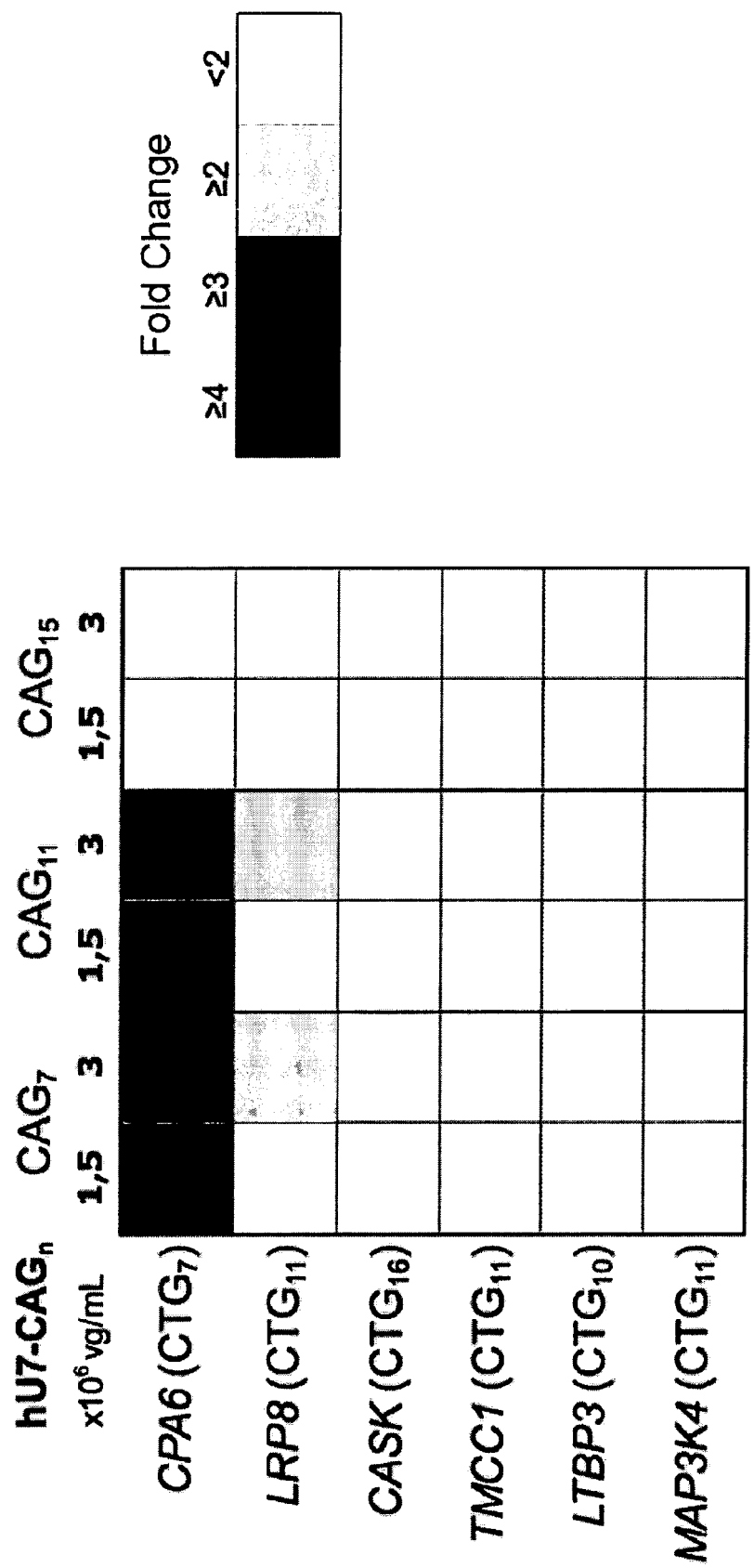
FIG. 7 Fold-change of off-target transcripts bearing CUG repeats was analyzed by RT-PCR in DM1 myoblasts (800 CTG) transduced with hU7-CAG$_n$ lentiviral vectors expressing antisense sequences of 7, 11 or 15 CAG.
Figure 8:
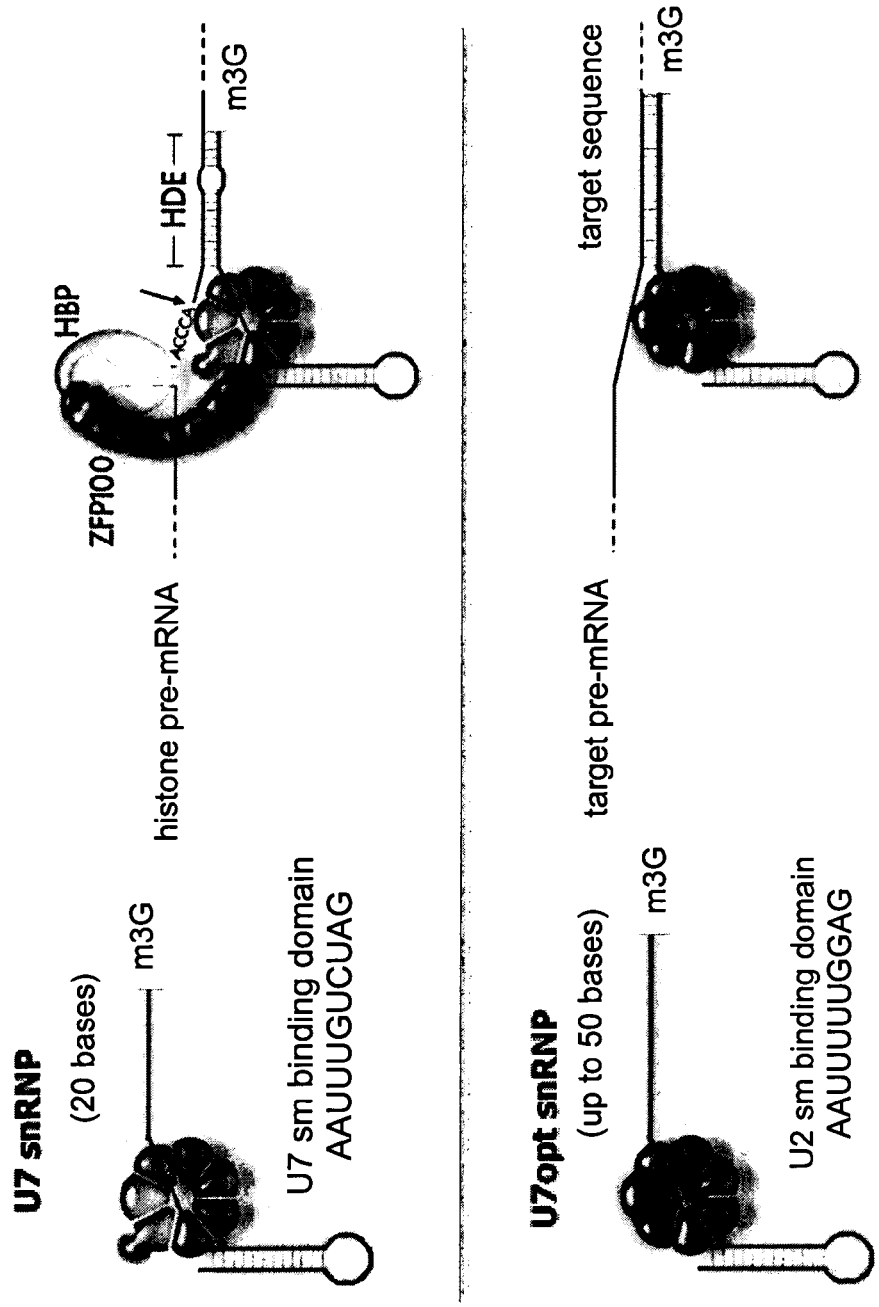
FIG. 8 Schematic representation of U7 and U7smOPT
Figure 9:
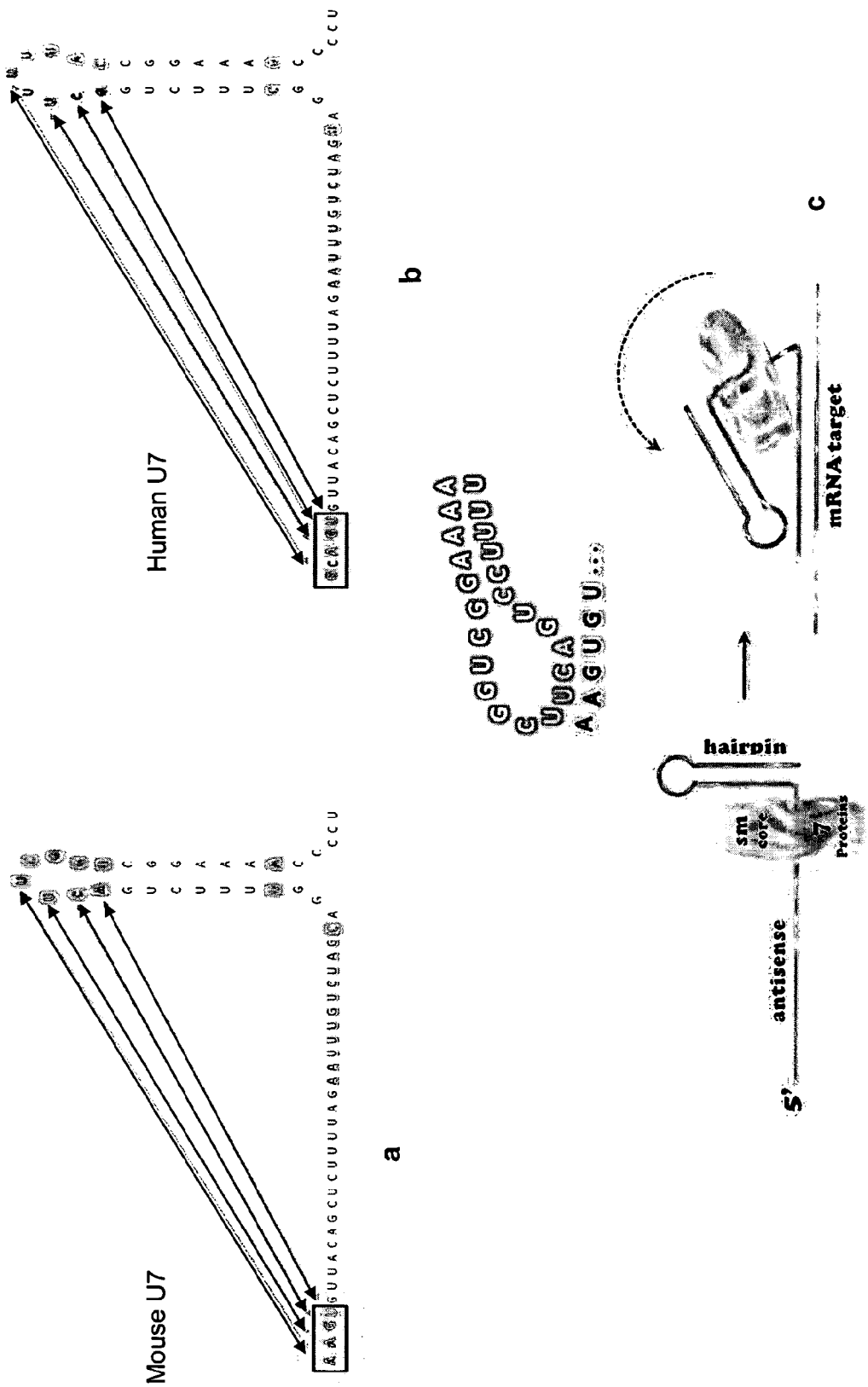
FIG. 9 (a) wild-type mouse U7; (b) wild-type human U7; (c) hypothetical folding for U7smOPT: need of a "kissing domain."

Muscle cells isolated from DM1 patients with a choice of CTG expansions were transduced with lentiviral vectors expressing an optimized hU7-$CAG_{15}$ (15 CAG repeats). In these cells, the normal allele displayed less than 37 repeats while mutant alleles exhibited CTG expansions ranging from 200 to 2000 repeats. Transduced cells were kept growing for at least one week before assessing DMPK mRNAs stability. Northern blot analysis showed that the steady-state levels of expanded DMPK transcripts were significantly (P<0.001) reduced by 71 to 82% in DM1 cells expressing hU7-$CAG_{15}$ (FIG. 1b). Disappearance of expanded DMPK mRNAs occurred in a vector dose-dependant manner (FIG. 4a). Importantly, the normal DMPK mRNA was preserved. This phenomenon was also confirmed in wild-type myoblasts bearing 13/18 CTG repeats (FIG. 5). Moreover, the alternative splicing of the normal DMPK isoform E14/16 (Tiscornia et al., Mol Cell, 5: 959-967, 2000), lacking both exon 15 and CUG tract, was not affected by hU7-$CAG_{15}$ (FIG. 6a) and no change in DMPK protein levels were observed in treated-DM1 cells (FIG. 6b). It is also noteworthy that the use of the hU7-$CAG_n$ system allowed maintaining continuous and permanent targeted destruction of the deleterious transcripts over cell passages.

To further assess the disappearance of mutated DMPK mRNAs, we examined the $CUG^{exp}$ ribonucleoprotein complexes, which usually accumulate as numerous foci in DM1 nuclei. As expected, fluorescence in situ hybridization (FISH) analysis showed a dose-dependent dramatic loss of these nuclear structures in treated DM1 myoblasts (FIG. 1c and FIG. 24b). Up to 60% of the hU7-$CAG_{15}$ treated DM1 myoblasts displayed no foci (P<0.001). Additional 25% of this cell population only displayed a single faint focus. In addition, no remaining foci were observed in the cytoplasmic compartment. Nuclear and cytoplasmic RNA fractionation of DM1 cells containing a polymorphic restriction site on the expanded allele (Hamshere et al., *Proc Natl Acad Sci USA*, 94: 7394-7399, 1997) confirmed that mutated transcripts are retained in the nucleus and are not exported to the cytoplasm (FIG. 1d). In the presence of hU7-$CAG_{15}$, no transcripts from the $CTG^{exp}$ allele were detected in the cytoplasmic fraction demonstrating the presence of a mechanism of selective degradation of the $CUG^{exp}$-mRNAs in the nucleus. Strikingly, this mechanism did not concern DMPK mRNAs, suggesting that hU7-$CAG_{15}$ operated at the level of foci rather than at the level of mRNA genesis.

Figures 2A, 2B:
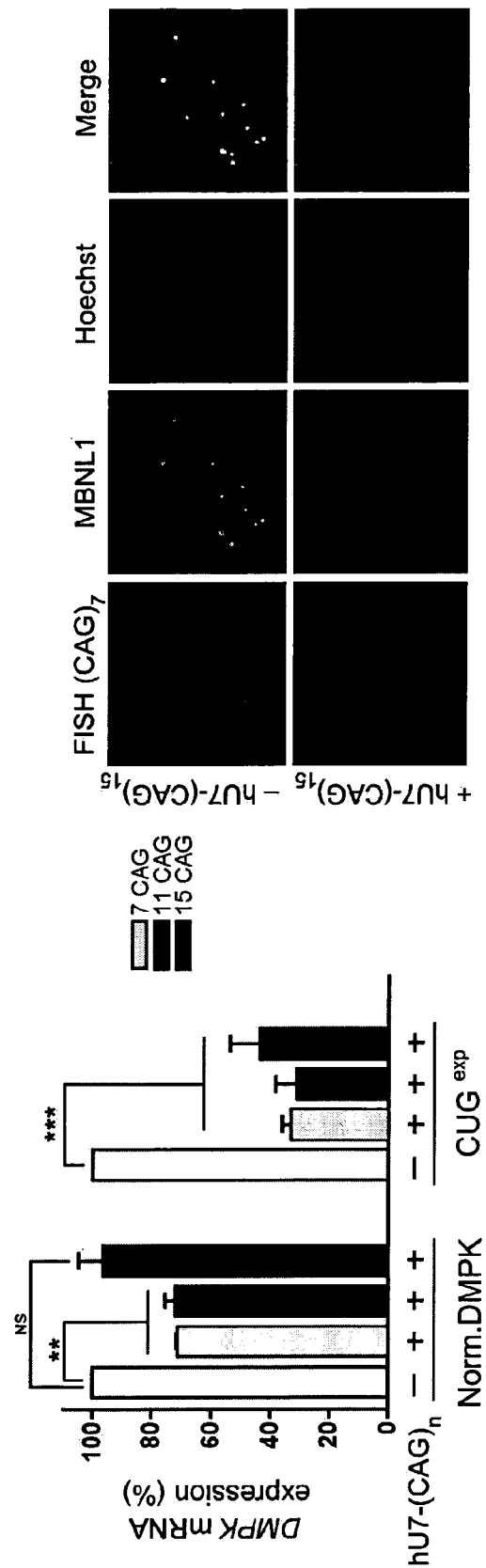
FIG. 2 Consequences of hU7-CAG$_n$ expression in DM1 muscle cells (a) Expression of normal and CUG$^{exp}$ DMPK mRNAs in DM1 cells (13/800 CTG) transduced with hU7-CAG$_n$ vectors (4×106 vg/mL) harboring antisense sequences of 7, 11 or 15 CAG (n=3). (b) Localization of the splicing regulator MBNL1 in DM1 cells. (c) Correction of alternative splicing misregulation of BIN1 (bridging integrator1), DMD (dystrophin) and LDB3 (cypher) transcripts in differentiated DM1 muscle cells (2000 CTG) (n=3). (d) Myogenic differentiation of DM1 muscle cells (2000 CTG) quantified as fusion index (n=6).

In order to evaluate the effect of the length of the CAG antisense sequence, we designed additional hU7-snRNA constructs harboring shortened CAG sequences (7 and 11 repeats). All of them targeted and silenced efficiently $CUG^{exp}$-DMPK mRNAs (P<0.001) in DM1 cells. However, these shortened constructs also affected the product of the normal DMPK allele (P<0.01), which contained 13 CUG repeats (FIG. 2a). Such a loss of specificity prompted us to analyze six human transcripts also bearing CUG tracts ranging from 7 to 16 repeats (FIG. 6). Four of these gene products were unaffected in DM1 cells expressing hU7-$CAG7_{either\ 11\ or\ 15}$. Nevertheless, altered expressions of CPA6 (7 CUG) and LRP8 (11 CUG) transcripts were correlated with the decrease of the length of the CAG antisense sequence. Importantly, the larger $CAG_{15}$ did not significantly affect either CPA6 or LRP8.

We then assessed whether hU7-$CAG_{15}$ was able to reverse pathophysiological consequences of toxic $CUG^{exp}$-mRNAs. We focused on DM1 hallmarks such as MBNL1 sequestration and abnormal regulation of alternative splicing. Combined FISH-immunofluorescence analysis showed that silencing $CUG^{exp}$-mRNAs lead to the release of sequestered MBNL1 from the nuclear $CUG^{exp}$-aggregates and a normal relocation of MBNL1 in treated DM1 cells (FIG. 2b).

Figure 2C:
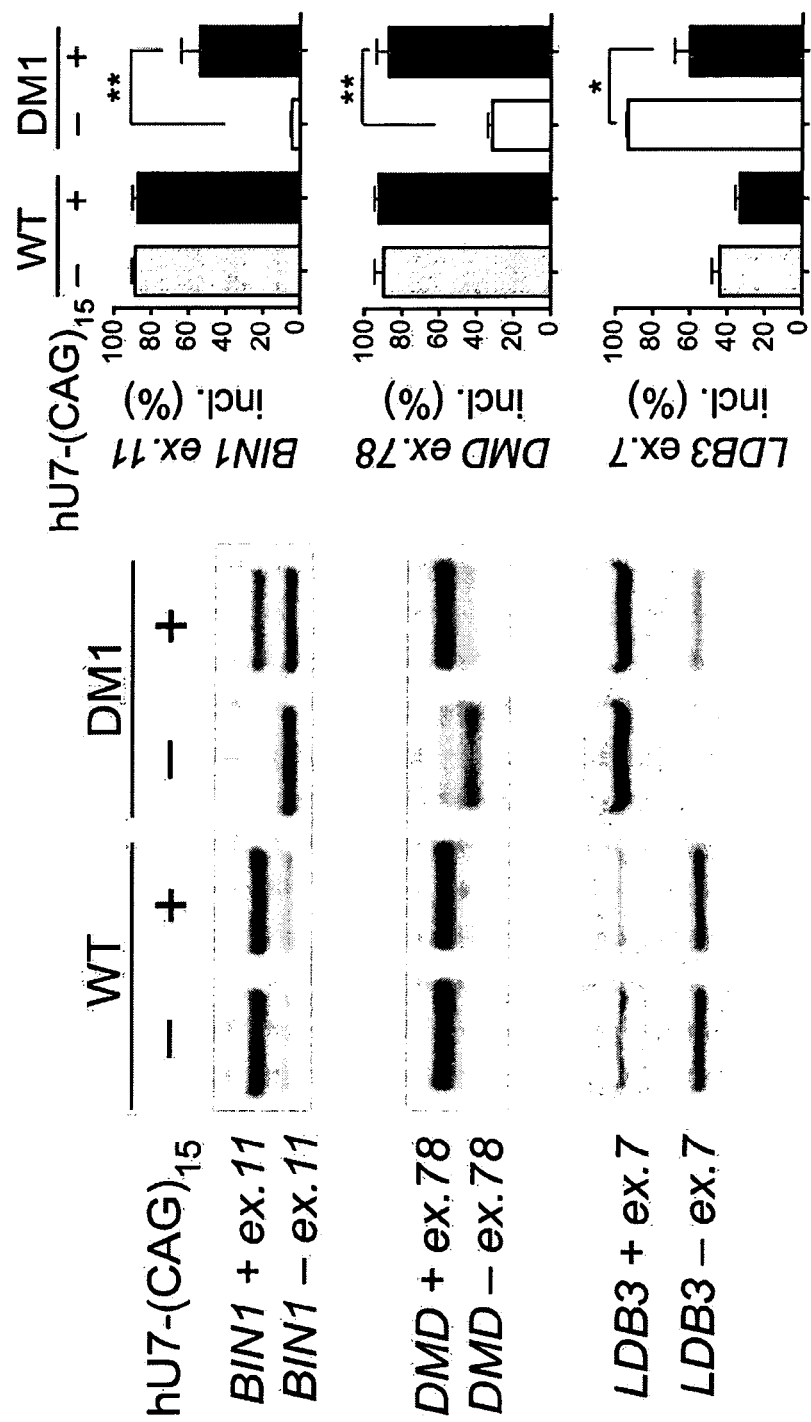
Figure 2D:
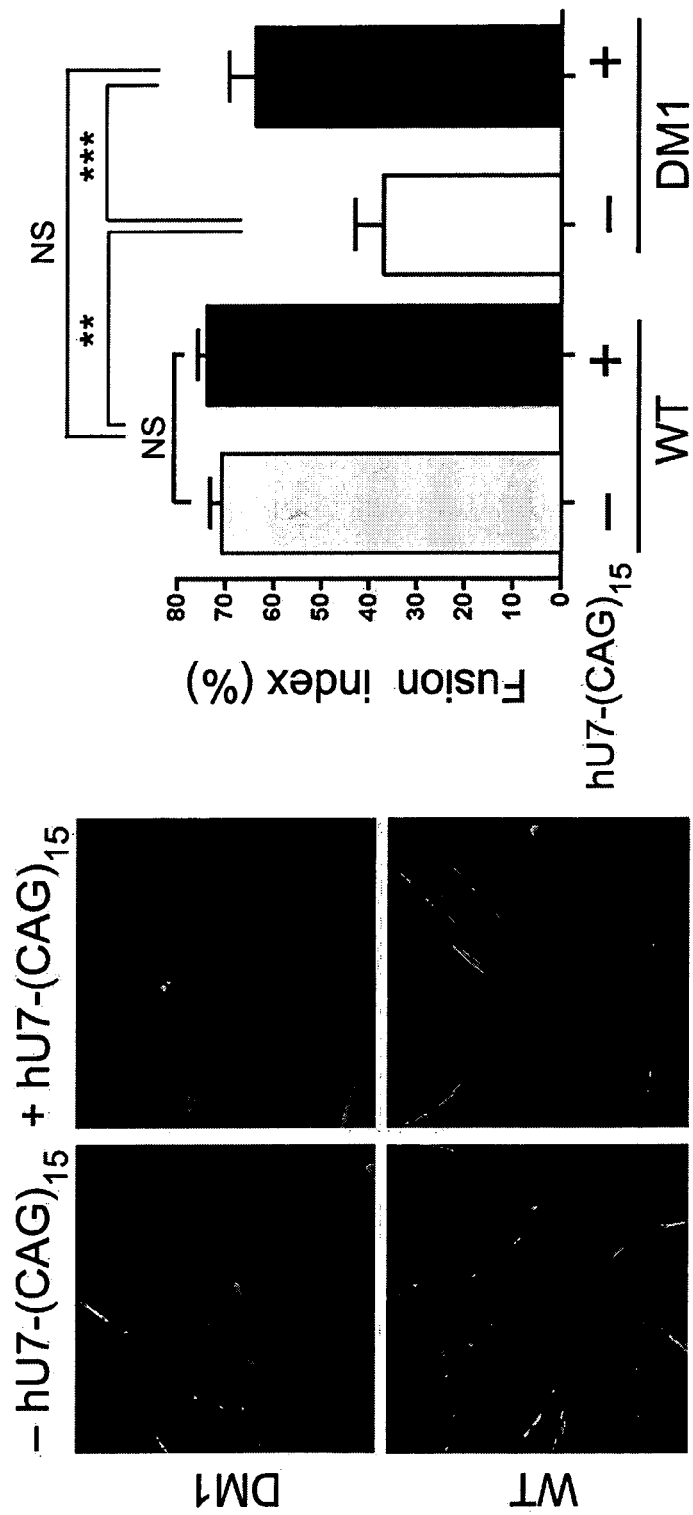

The outcome on DM1 splicing misregulation was examined on several genes, such as BIN1, DMD and LDB3, which are abnormally spliced in differentiated DM1 muscle cells. Splicing profiles of these genes were significantly (P<0.01) normalized in the presence of hU7-$CAG_{15}$, while hU7-$CAG_{15}$ did not affect the splicing of these genes in wild-type cells (FIG. 2c). It is also known that DM1 muscle cells with large CTG expansions display defective differentiation (Furling et al., *Hum Mol Genet*, 10: 2079-2087, 2001) (P<0.001). Here, in the presence of hU7-CAG$_{15}$, the fusion index of treated-DM1 myoblasts was appreciably restored (P<0.01) to a level similar to that of wild-type myoblasts (FIG. 2e).

In conclusion, our data show that the U7-CAG system allowed long-lasting selective destruction of deleterious CUG$^{exp}$-mRNAs. MBNL1 and likely other mRNA binding factors were subsequently released from foci, leading to improved splicing and differentiation in treated DM1 cells. The length of the CAG antisense sequence seems critical. Below 15 CAG repeats, the occurrence of off-targets might counterbalance the benefit provided by the destruction of mutated mRNAs. The very mechanism by which the U7-CAG$_{15}$ triggered selective destruction of CUG$^{exp}$-mRNAs is not fully determined. Engineered U7-snRNAs as well as morpholinos and 2'-O-methyl phosphorothioates, which have been successfully applied in DM1 (Wheeler et al., *Science*, 325: 336-339, 2009; Mulders et al., *Proc Natl Acad Sci USA*, 106: 13915-13920, 2009), are not supposed to trigger RNase activities. On the contrary, these compounds are commonly used to force alternative splicing in both exon skipping and exon inclusion strategies (Du & Gatti, *Curr Opin Mol Ther*, 11(2):116-23, 2009). It is likely that the selective destruction of CUG$^{exp}$-DMPK mRNAs in the presence of CAG antisense molecules is not based on canonical RNA interference mechanisms. Rather, disappearance or accelerated nuclear decay of CUG$^{exp}$-DMPK/CAG$_n$ heteroduplexes would be due to innate instability of the mutant DMPK mRNAs, a phenomenon unfortunately counteracted by MBNL1 in untreated DM1 cells.

Delineation of the Kiss Domain.
Materials and Methods
Mice and AAV Injections.

All animal procedures were performed according to an institution-approved protocol and under appropriate biological containment. Eight-week-old mdx mice were injected with 50 μL phosphate-buffered saline containing AAV vectors into the TA (see Table 1). After one month the mice were killed and the muscles were collected, snap-frozen in liquid nitrogen-cooled isopentane, and stored at −80° C.

Constructs and Recombinants AAV Vectors

The reference construct AAV_U7_SD23/BP22 was previously described in WO 2006/021724. For modified constructs, 1 to 4 base-pairs are changed by mutagenesis PCR (Stratagene) in the U7 loop or in the antisense sequence corresponding to the hypothetic loop binding (see Table 2 for sequences details). AAV2/1 pseudotyped vectors were prepared by transfection in 293 cells as described and vector particles were purified on caesium chloride gradients from cell lysates obtained 48 hours after transfection and tittered by quantitative dot blot hybridization. Titers are given in Table 1.

Histology

A series of 8-μm transverse sections cut at 200-μm intervals over the muscle length, were examined for dystrophin (NCL-DYS2 monoclonal antibody to the C-terminal domain, NovoCastra) by immunohistochemistry. Mounted sections were analyzed by confocal laser microscopy (Leica). Intermediate tissue was collected for mRNA analysis.

RNA Analysis

Total RNA was isolated from pooled intermediate sections using TRIzol-reagent (Life Technologies). To detect dystrophin mRNA, reverse transcription was first performed on total RNA with Superscript II reverse transcriptase in the presence of random hexamers (Invitrogen). Then, nested PCR was performed on the cDNA by using PCR Master Mix (Promega). The first reaction was performed with Ex20ext (SEQ ID NO: 33: 5'-CAGAATTCTGCCAATTGCTGAG-3') and Ex26ext (SEQ ID NO: 34: 5'-TTCTTCAGCTTGTGTCATCC-3') primers for 30 cycles (94° C./30 s; 55° C./1 min; 72° C./2 min). Then 2 μL of the first reaction were amplified for 25 cycles with Ex20int (SEQ ID NO: 35: 5'-CCCAGTCTACCACCCTATCAGAGC-3') and Ex26int (SEQ ID NO: 36: 5'-CCTGCCTTTAAGGCTTCCTT-3'). PCR products were analyzed on 2% agarose gels Results The following section describes experiments showing the need of a kiss domain to achieve dystrophin rescue by using U7smOPT-exon skipping in the mdx mouse model. The mdx mouse (Bulfield et al., 1984; Ryder-Cook et al., 1988) has a single base substitution within exon 23 of the dystrophin gene, which causes premature termination of the polypeptide chain (Sicinski et al., 1989) so the full-length 427 KDa muscle isoform of dystrophin is not produced. Accordingly to the exon phasing of the dystrophin gene, translation of a shortened-dystrophin (quasi-dystrophin) could be possible by skipping exon 23 in the course of the mRNA splicing.

Figure 10:
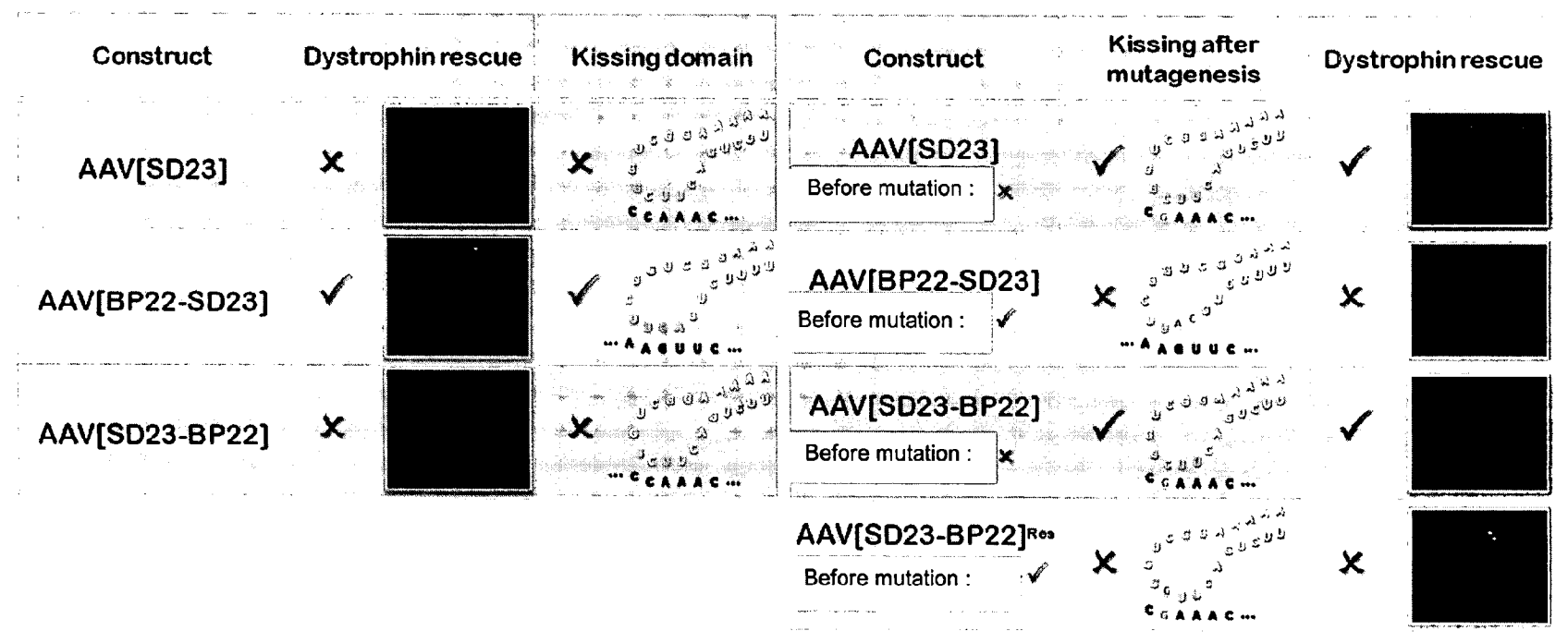

A number of antisense sequences were designed to skip the nonsense mutation containing exon 23 on the mdx dystrophin mRNA. These sequences were associated with U7smOPT and introduced into AAV2-based vectors that were packaged into AAV1 capsid for high efficiency gene transfer into skeletal muscle. Adult mdx mice were injected in the tibialis anterior (TA) muscle with single vector doses of about 10E12 viral genomes, and dystrophin rescue was assayed one month later (FIG. 10). Only the constructs allowing an interaction between the kiss domain and the loop are efficient in rescuing dystrophin.

TABLE 1

AAV constructions

| mice | TAD | TAG | AAV dose (vg/ml) | | FIGS. |
|---|---|---|---|---|---|
| 3 | AAV_U7_BP22/SD23 | AAV_U7_BP22/SD23 modif | $2 \times 10^{12}$ | $1.4 \times 10^{13}$ | A/A' |
| 3 | AAV_U7_BP22/SD23modif | AAV_U7_BP22/SD23-2X modif | $1.4 \times 10^{13}$ | $1.4 \times 10^{12}$ | B/B' |
| 3 | AAV_U7_SD23 | AAV_U7_SD23 modif | $2.8 \times 10^{12}$ | $8.2 \times 10^{11}$ | C/C' |
| 3 | AAV_U7_SD23/BP22 (ref) | AAV_U7_SD23/BP22_loop modif | $4.5 \times 10^{12}$ | $5.2 \times 10^{12}$ | D/D' |
| 4 | AAV_U7_SD23/BP22 (ref) | AAV_U7_SD23/BP22_new loop | $4.5 \times 10^{12}$ | $2.3 \times 10^{12}$ | |
| 4 | AAV_U7_BP22/SD23_loop modif | AAV_U7_BP22/SD23 modif | $3 \times 10^{12}$ | $1.4 \times 10^{13}$ | |

TABLE 2

| Name of constructions | Sequences |
|---|---|
| AAV_U7_BP22/SD23 | BP22: 5'-AAATAGAAGTTCATTTACACTAAC-3' (SEQ ID NO: 37) |

TABLE 2-continued

| Name of constructions | Sequences |
|---|---|
| | SD23: 5'-GGCCAAACCTCGGCTTACCT-3' (SEQ ID NO: 38) |
| AAV_U7_BP22/SD23modif | BP22: 5'-AAATAGAAGTTCATTTACACTAAC-3' (SEQ ID NO: 37)<br>SD23 modif: 5'-GGCGAAACCTCGGCTTACCT-3' (SEQ ID NO: 39) |
| AAV_U7_BP22/SD23_loop modif | Smopt-loop: 5'-AATTTTTGGAGCAGGTTTTCTGACTTGGGTCGGAAAACC-3' (SEQ ID NO: 40) |
| AAV_U7_BP22/SD23-2X modif | BP22: 5'-AAATAGAAGTTCATTTACACTAAC-3' (SEQ ID NO: 37)<br>SD23: 5'-GGCGAAACCTCGGCTTACCT-3' (SEQ ID NO: 38)<br>Smopt-loop: 5'-AATTTTTGGAGCAGGTTTTCTGACTTGGGTCGGAAAACC-3' (SEQ ID NO: 40) |
| AAV_U7_SD23 modif | SD23: 5'-GGCGAAACCTCGGCTTACCT-3' (SEQ ID NO: 38) |
| AAV_U7_SD23/BP22_loop modif | Smopt-loop modif: 5'-AATTTTTGGAGCAGGTTTTCTGACGGCGTCGGAAAACC-3' (SEQ ID NO: 41) |
| AAV_U7_SD23/BP22_new loop | Smopt-loop modif2: 5'-AATTTTTGGAGCAGGTTTTCTGCAGGCGTCGGAAAACC-3' (SEQ ID NO: 42) |

The invention claimed is:

1. A modified huU7 snRNA, comprising the following elements bound covalently in the following order, from the 3' end to the 5' end:
 a polynucleotide having the sequence of SEQ ID NO: 1,
 a SmOPT domain having the sequence of SEQ ID NO: 2, and
 at least one polynucleotide, said polynucleotide being capable of hybridizing with at least part of a target pre-mRNA, and
 a kiss domain comprising at least three nucleotides,
 wherein said kiss domain hybridizes with at least three nucleotides of the U7 loop,
 wherein said U7 loop consists of nucleotides 12-20 of SEQ ID NO: 1.

2. The modified huU7 snRNA of claim 1, wherein the said at least part of a target pre-mRNA is at least one splice site of one exon.

3. The modified huU7 snRNA of claim 2, wherein the splice site is chosen from the group consisting of the 5' donor site, the 3' acceptor site, the branch point (BP) sequence, the exonic-splicing enhancer (ESE) sequence, the intronic-splicing enhancer (ISE) sequence, and the intronic silencer sequences (ISS) and the terminal stem loop (TSL).

4. The modified huU7 snRNA of claim 1, wherein the at least part of a target pre-mRNA is a trinucleotide repeat expansion.

5. The modified huU7 snRNA of claim 4, wherein the trinucleotide is CUG.

6. The modified huU7 snRNA of claim 4, wherein the antisense comprises at least 15 repeats of the trinucleotide CAG.

7. The modified huU7 snRNA of claim 1, wherein the said kiss domain has a sequence chosen between AAGU, GAGU, GGGU and AGGU or the said kiss domain has a sequence chosen between GCAGU, GAAGU, GCGGU, GGAGU, GAGGU and GGGGU.

8. A polynucleotide comprising a gene coding the modified huU7 snRNA of claim 1.

9. The polynucleotide of claim 8, wherein the said gene is fused to regulatory sequences.

10. The polynucleotide of claim 9, wherein the said regulatory sequences comprise the human U7 promoter.

11. The polynucleotide of claim 10, wherein the said promoter has the sequence of SEQ ID NO. 3.

12. The polynucleotide of claim 9, wherein the said regulatory sequences comprise the huU7 snRNA gene downstream sequence.

13. The polynucleotide of claim 12, wherein the said downstream sequence have the sequence of SEQ ID NO: 4.

14. A vector comprising the polynucleotide of claim 8.

15. The vector of claim 14, wherein said vector is chosen in the group consisting of plasmids, adenoviral vectors, associated-adenoviral vectors and lentiviral vectors.

16. An isolated eukaryotic cell transfected by the vector of claim 14.

17. The cell of claim 16, wherein the said cell is a skeletal muscle cell, a myoblast or a cell capable of muscle differentiation.

18. The cell of claim 16, wherein said cell is an induced pluripotent stem cell.

19. A pharmaceutical composition comprising the vector of claim 14 or the cell of claim 16.

20. A method for treating or preventing a neuromuscular disease, the said method comprising the step of administering the vector of claim 14 or the cell of claim 16, and the said neuromuscular disease being selected in the group consisting of: Duchenne muscular dystrophy, Becker muscular dystrophy, limb girdle muscular dystrophy, congenital muscular dystrophy, facioscapulohumeral muscular dystrophy, myotonic muscular dystrophy, oculopharyngeal muscular dystrophy, distal muscular dystrophy, Emery-Dreifuss muscular dystrophy, and spinal muscular atrophy.

21. The method of claim 20, wherein the neuromuscular disease is a neuromuscular dystrophy.

22. The method of claim 21, wherein the neuromuscular dystrophy is Duchenne muscular dystrophy or myotonic dystrophy 1.

23. The method of claim 20, wherein the neuromuscular disease is spinal muscular atrophy.

24. A method for restoring the function of a cellular protein by exon skipping, exon inclusion, or eradication of deleterious mRNAs, comprising the step of contacting a cell with the vector of claim 14.

* * * * *

SEQUENCE LISTING

<160> NUMBER OF SEQ ID NOS: 42

<210> SEQ ID NO 1
<211> LENGTH: 32
<212> TYPE: RNA
<213> ORGANISM: Homo sapiens
<220> FEATURE:
<221> NAME/KEY: misc_feature
<223> OTHER INFORMATION: huU7 snRNA stem/loop

<400> SEQUENCE: 1
uaggcuuucu ggcuuuuuac cggaaagccc cu         32

<210> SEQ ID NO 2
<211> LENGTH: 11
<212> TYPE: RNA
<213> ORGANISM: Homo sapiens
<220> FEATURE:
<221> NAME/KEY: misc_feature
<223> OTHER INFORMATION: smOPT

<400> SEQUENCE: 2
aauuuuugga g         11

<210> SEQ ID NO 3
<211> LENGTH: 363
<212> TYPE: DNA
<213> ORGANISM: Homo sapiens
<220> FEATURE:
<221> NAME/KEY: misc_feature
<223> OTHER INFORMATION: huU7 promoter

<400> SEQUENCE: 3
gggcattagg ctccatcgct catcaataga caaggccttt aggaaactgc gacaacggct      60
tttgctctgg gcctttactg ccgaatccag gtctccgggc ttaacaacaa cgaagggggct    120 gtgactggct gctttctcaa ccaatcagca ccgaactcat ttgcatgggc tgagaacaaa    180
tgttcgcgaa ctctagaaat gaatgactta agtaagttcc ttagaatatt attttcctta   240
ctgaaagtta ccacatgcgt cgttgtttat acagtaataag gaacaagaaa aaagtcacct    300
aagctcaccc tcatcaattg tggagttcct ttatatccca tcttctctcc aaacacatac   360

| gca | 363 |

<210> SEQ ID NO 4
<211> LENGTH: 233
<212> TYPE: DNA
<213> ORGANISM: Homo sapiens
<220> FEATURE:
<221> NAME/KEY: misc_feature
<223> OTHER INFORMATION: huU7 downstream elements

<400> SEQUENCE: 4

| cttatgatgt tgttgccaa tgatagattg ttttcactgt gcaaaaatta tgggtagttt | 60 |
| tggtggtctt gatgcagttg taagcttggg gtatgaaggt ttgggccacg cctgggcgct | 120 |
| tccggctgcg ccggatgctg tttcctttcc gctcccaggg gcgttgggaa cggttgtagg | 180 |
| acgtggctct ttattcgtga gttttccatt tacctccgct gaacctagag ctt | 233 |

<210> SEQ ID NO 5
<211> LENGTH: 26
<212> TYPE: DNA
<213> ORGANISM: Artificial Sequence
<220> FEATURE:
<223> OTHER INFORMATION: GAPDH-F oligo

<400> SEQUENCE: 5

| tgaaggtcgg agtcaacgga tttggt | 26 |

<210> SEQ ID NO 6
<211> LENGTH: 25
<212> TYPE: DNA
<213> ORGANISM: Artificial Sequence
<220> FEATURE:
<223> OTHER INFORMATION: GAPDH-R oligo

<400> SEQUENCE: 6

| gatgacaagc ttcccgttct cagcc | 25 |

<210> SEQ ID NO 7
<211> LENGTH: 17
<212> TYPE: DNA
<213> ORGANISM: Artificial Sequence
<220> FEATURE:
<223> OTHER INFORMATION: U6snRNA-F oligo

<400> SEQUENCE: 7

| ctcgcttcgg cagcaca | 17 |

<210> SEQ ID NO 8
<211> LENGTH: 20
<212> TYPE: DNA
<213> ORGANISM: Artificial Sequence
<220> FEATURE:
<223> OTHER INFORMATION: U6snRNA-R oligo

<400> SEQUENCE: 8

| aacgcttcac gaatttgcgt | 20 |

<210> SEQ ID NO 9
<211> LENGTH: 25
<212> TYPE: DNA
<213> ORGANISM: Artificial Sequence
<220> FEATURE:
<223> OTHER INFORMATION: DMPK exon 9-exon 10-F oligo

<400> SEQUENCE: 9

-continued

```
cactgtcgga cattcgggaa ggtgc                                      25

<210> SEQ ID NO 10
<211> LENGTH: 26
<212> TYPE: DNA
<213> ORGANISM: Artificial Sequence
<220> FEATURE:
<223> OTHER INFORMATION: DMPK exon 9-exon 10-R oligo

<400> SEQUENCE: 10
gcttgcacgt gtggctcaag cagctg                                     26

<210> SEQ ID NO 11
<211> LENGTH: 20
<212> TYPE: DNA
<213> ORGANISM: Artificial Sequence
<220> FEATURE:
<223> OTHER INFORMATION: DMPK intron 9-intron 10-F oligo

<400> SEQUENCE: 11
ctacccacag gccagaagtt                                            20

<210> SEQ ID NO 12
<211> LENGTH: 20
<212> TYPE: DNA
<213> ORGANISM: Artificial Sequence
<220> FEATURE:
<223> OTHER INFORMATION: DMPK intron 9-intron 10-R oligo

<400> SEQUENCE: 12
ggaagccctc accttttctc                                            20

<210> SEQ ID NO 13
<211> LENGTH: 20
<212> TYPE: DNA
<213> ORGANISM: Artificial Sequence
<220> FEATURE:
<223> OTHER INFORMATION: DMPK splice junction exon 14/16-exon 16-F oligo

<400> SEQUENCE: 13
ctgctccctg ccagggctga                                            20

<210> SEQ ID NO 14
<211> LENGTH: 22
<212> TYPE: DNA
<213> ORGANISM: Artificial Sequence
<220> FEATURE:
<223> OTHER INFORMATION: DMPK splice junction exon 14/16-exon 16-R oligo

<400> SEQUENCE: 14
tgtcggggtc tcagtgcatc ca                                         22

<210> SEQ ID NO 15
<211> LENGTH: 20
<212> TYPE: DNA
<213> ORGANISM: Artificial Sequence
<220> FEATURE:
<223> OTHER INFORMATION: CPA6-F oligo

<400> SEQUENCE: 15
actgatgtcc atatccccca                                            20

<210> SEQ ID NO 16
<211> LENGTH: 20
<212> TYPE: DNA
<213> ORGANISM: Artificial Sequence
```

```
<220> FEATURE:
<223> OTHER INFORMATION: CPA6-R oligo

<400> SEQUENCE: 16
tttgagtcgt gatcgtctgc                                               20

<210> SEQ ID NO 17
<211> LENGTH: 20
<212> TYPE: DNA
<213> ORGANISM: Artificial Sequence
<220> FEATURE:
<223> OTHER INFORMATION: LTBP3-F oligo

<400> SEQUENCE: 17
gagaagagcc tgtgtttccg                                               20

<210> SEQ ID NO 18
<211> LENGTH: 20
<212> TYPE: DNA
<213> ORGANISM: Artificial Sequence
<220> FEATURE:
<223> OTHER INFORMATION: LTBP3-R oligo

<400> SEQUENCE: 18
gaaaagtcac tctcgccctg                                               20

<210> SEQ ID NO 19
<211> LENGTH: 20
<212> TYPE: DNA
<213> ORGANISM: Artificial Sequence
<220> FEATURE:
<223> OTHER INFORMATION: LRP8-F oligo

<400> SEQUENCE: 19
ctccactgac ttcctgagcc                                               20

<210> SEQ ID NO 20
<211> LENGTH: 20
<212> TYPE: DNA
<213> ORGANISM: Artificial Sequence
<220> FEATURE:
<223> OTHER INFORMATION: LRP8-R oligo

<400> SEQUENCE: 20
gtgctcggta gcacctcttc                                               20

<210> SEQ ID NO 21
<211> LENGTH: 20
<212> TYPE: DNA
<213> ORGANISM: Artificial Sequence
<220> FEATURE:
<223> OTHER INFORMATION: TMCC1-F oligo

<400> SEQUENCE: 21
gagcaaaggt gactggcttc                                               20

<210> SEQ ID NO 22
<211> LENGTH: 20
<212> TYPE: DNA
<213> ORGANISM: Artificial Sequence
<220> FEATURE:
<223> OTHER INFORMATION: TMCC1-R oligo

<400> SEQUENCE: 22
cgctcctcct gtaaggtctg                                               20
```

<210> SEQ ID NO 23
<211> LENGTH: 20
<212> TYPE: DNA
<213> ORGANISM: Artificial Sequence
<220> FEATURE:
<223> OTHER INFORMATION: CASK-F oligo

<400> SEQUENCE: 23
cagagttcgg ctggtacagt                                               20

<210> SEQ ID NO 24
<211> LENGTH: 20
<212> TYPE: DNA
<213> ORGANISM: Artificial Sequence
<220> FEATURE:
<223> OTHER INFORMATION: CASK-R oligo

<400> SEQUENCE: 24
acaggacgaa gactgagtgc                                               20

<210> SEQ ID NO 25
<211> LENGTH: 20
<212> TYPE: DNA
<213> ORGANISM: Artificial Sequence
<220> FEATURE:
<223> OTHER INFORMATION: MAP3K4-F oligo

<400> SEQUENCE: 25
aagggcacgt atagcattgg                                               20

<210> SEQ ID NO 26
<211> LENGTH: 20
<212> TYPE: DNA
<213> ORGANISM: Artificial Sequence
<220> FEATURE:
<223> OTHER INFORMATION: MAP3K4-R oligo

<400> SEQUENCE: 26
tggttctcca gcaggtctct                                               20

<210> SEQ ID NO 27
<211> LENGTH: 21
<212> TYPE: DNA
<213> ORGANISM: Artificial Sequence
<220> FEATURE:
<223> OTHER INFORMATION: BIN1-exon 11-F oligo

<400> SEQUENCE: 27
agaacctcaa tgatgtgctg g                                             21

<210> SEQ ID NO 28
<211> LENGTH: 22
<212> TYPE: DNA
<213> ORGANISM: Artificial Sequence
<220> FEATURE:
<223> OTHER INFORMATION: BIN1-exon 11-R oligo

<400> SEQUENCE: 28
tcgtggttga ctctgatctc gg                                            22

<210> SEQ ID NO 29
<211> LENGTH: 20
<212> TYPE: DNA
<213> ORGANISM: Artificial Sequence
<220> FEATURE:
<223> OTHER INFORMATION: DMD-exon 78-F oligo -continued

```
<400> SEQUENCE: 29
ttagaggagg tgatggagca                                               20

<210> SEQ ID NO 30
<211> LENGTH: 20
<212> TYPE: DNA
<213> ORGANISM: Artificial Sequence
<220> FEATURE:
<223> OTHER INFORMATION: DMD-exon 78-R oligo

<400> SEQUENCE: 30
gatactaagg actccatcgc                                               20

<210> SEQ ID NO 31
<211> LENGTH: 23
<212> TYPE: DNA
<213> ORGANISM: Artificial Sequence
<220> FEATURE:
<223> OTHER INFORMATION: LDB3-exon 7-F oligo

<400> SEQUENCE: 31
gcaagaccct gatgaagaag ctc                                           23

<210> SEQ ID NO 32
<211> LENGTH: 19
<212> TYPE: DNA
<213> ORGANISM: Artificial Sequence
<220> FEATURE:
<223> OTHER INFORMATION: LDB3-exon 7-R oligo

<400> SEQUENCE: 32
gacagaaggc cggatgctg                                                19

<210> SEQ ID NO 33
<211> LENGTH: 22
<212> TYPE: DNA
<213> ORGANISM: Artificial Sequence
<220> FEATURE:
<223> OTHER INFORMATION: Ex20ext oligo

<400> SEQUENCE: 33
cagaattctg ccaattgctg ag                                            22

<210> SEQ ID NO 34
<211> LENGTH: 20
<212> TYPE: DNA
<213> ORGANISM: Artificial Sequence
<220> FEATURE:
<223> OTHER INFORMATION: Ex26ext oligo

<400> SEQUENCE: 34
ttcttcagct tgtgtcatcc                                               20

<210> SEQ ID NO 35
<211> LENGTH: 24
<212> TYPE: DNA
<213> ORGANISM: Artificial Sequence
<220> FEATURE:
<223> OTHER INFORMATION: Ex20int oligo

<400> SEQUENCE: 35
cccagtctac caccctatca gagc                                          24

<210> SEQ ID NO 36
```

```
<211> LENGTH: 20
<212> TYPE: DNA
<213> ORGANISM: Artificial Sequence
<220> FEATURE:
<223> OTHER INFORMATION: Ex26int oligo

<400> SEQUENCE: 36
cctgccttta aggcttcctt                                              20

<210> SEQ ID NO 37
<211> LENGTH: 24
<212> TYPE: DNA
<213> ORGANISM: Artificial Sequence
<220> FEATURE:
<223> OTHER INFORMATION: BP22 oligo

<400> SEQUENCE: 37
aaatagaagt tcatttacac taac                                         24

<210> SEQ ID NO 38
<211> LENGTH: 20
<212> TYPE: DNA
<213> ORGANISM: Artificial Sequence
<220> FEATURE:
<223> OTHER INFORMATION: SD23 oligo

<400> SEQUENCE: 38
ggccaaacct cggcttacct                                              20

<210> SEQ ID NO 39
<211> LENGTH: 20
<212> TYPE: DNA
<213> ORGANISM: Artificial Sequence
<220> FEATURE:
<223> OTHER INFORMATION: SD23 modif oligo

<400> SEQUENCE: 39
ggcgaaacct cggcttacct                                              20

<210> SEQ ID NO 40
<211> LENGTH: 39
<212> TYPE: DNA
<213> ORGANISM: Artificial Sequence
<220> FEATURE:
<223> OTHER INFORMATION: Smopt-loop oligo

<400> SEQUENCE: 40
aatttttgga gcaggttttc tgacttgggt cggaaaacc                         39

<210> SEQ ID NO 41
<211> LENGTH: 38
<212> TYPE: DNA
<213> ORGANISM: Artificial Sequence
<220> FEATURE:
<223> OTHER INFORMATION: Smopt-loop modif oligo

<400> SEQUENCE: 41
aatttttgga gcaggttttc tgacggcgtc ggaaaacc                          38

<210> SEQ ID NO 42
<211> LENGTH: 38
<212> TYPE: DNA
<213> ORGANISM: Artificial Sequence
<220> FEATURE:
<223> OTHER INFORMATION: Smopt-loop modif2 oligo
```

```
<400> SEQUENCE: 42 aattttgga gcaggttttc tgcaggcgtc ggaaaacc                                    38
```